United States Patent
Bernotas et al.

(10) Patent No.: US 6,825,212 B2
(45) Date of Patent: Nov. 30, 2004

(54) 1-(AMINOALKYL)-3-SULFONYLAZAINDOLES AS 5-HYDROXYTRYPTAMINE-6 LIGANDS

(75) Inventors: Ronald Charles Bernotas, Bridgewater, NJ (US); Steven Edward Lenicek, Plainsboro, NJ (US); Schuyler A. Antane, Princeton Junction, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/453,010

(22) Filed: Jun. 3, 2003

(65) Prior Publication Data
US 2003/0236278 A1 Dec. 25, 2003

Related U.S. Application Data
(60) Provisional application No. 60/385,502, filed on Jun. 4, 2002.

(51) Int. Cl.[7] ............ A61K 31/437; C07D 471/02
(52) U.S. Cl. ............ 514/300; 546/113; 546/112; 514/299
(58) Field of Search ............... 514/300, 299; 546/113, 112

(56) References Cited

U.S. PATENT DOCUMENTS

| 4,654,360 A | 3/1987 | Greenhouse |
| 5,132,319 A | 7/1992 | Girard et al. |
| 5,444,056 A | 8/1995 | Gubin et al. |
| 6,194,410 B1 | 2/2001 | Bös et al. |
| 6,251,923 B1 | 6/2001 | Höfgen et al. |

FOREIGN PATENT DOCUMENTS

| GB | 2298421 A | 4/1996 |
| WO | WO 01/12629 A1 | 2/2001 |
| WO | WO 01/82909 A2 | 11/2001 |
| WO | WO 02/098857 A1 | 12/2002 |
| WO | WO 03/013510 A1 | 2/2003 |
| WO | WO 03/080608 A2 | 10/2003 |

OTHER PUBLICATIONS

Garcia, J. et al., Tetrahedron Letters, 1985, 26(15): 1827–1830.
Cuadro, A. M. et al., Synthetic Communications, 1991, 21(4):535–544.
Wojciechowski, K. and Makosza, M., Synthesis, 1986, 651–653.
Takahashi, M. and Suga, D., Synthesis, 1998, 986–990.
Yuching Tsai et al., Bioorganic & Medicinal Chemistry Letters, 2000, 10:2295–2299.
International Search Report for corresponding PCT application No. PCT/US03/17466.

*Primary Examiner*—Charanjit S. Aulakh
(74) *Attorney, Agent, or Firm*—Barbara L. Lences

(57) ABSTRACT

The present invention provides a compound of formula I and the use thereof for the therapeutic treatment of disorders relating to or affected by the 5-HT6 receptor.

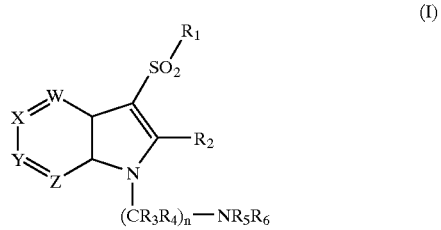

15 Claims, No Drawings

1-(AMINOALKYL)-3-SULFONYLAZAINDOLES AS 5-HYDROXYTRYPTAMINE-6 LIGANDS

This application claims priority from copending provisional application Ser. No. 60/385,502 filed Jun. 4, 2002, the entire disclosure of which is hereby incorporated by reference.

BACKGROUND OF THE INVENTION

Serotonin (5-Hydroxytryptamine)(5-HT) receptors play a critical role in many physiological and behavioral functions in humans and animals. These functions are mediated through various 5-HT receptors distributed throughout the body. There are now approximately fifteen different human 5-HT receptor subtypes that have been cloned, many with well-defined roles in humans. One of the most recently identified 5-HT receptor subtypes is the 5-HT6 receptor, first cloned from rat tissue in 1993 (Monsma, F. J.; Shen, Y.; Ward, R. P.; Hamblin, M. W. *Molecular Pharmacology* 1993, 43, 320–327) and subsequently from human tissue (Kohen, R.; Metcalf, M. A.; Khan, N.; Druck, T.; Huebner, K.; Sibley, D. R. *Journal of Neurochemistry* 1996, 66, 47–56). The receptor is a G-protein coupled receptor (GPCR) positively coupled to adenylate cyclase (Ruat, M.; Traiffort, E.; Arrang, J-M.; Tardivel-Lacombe, L.; Diaz, L.; Leurs, R.; Schwartz, J-C. *Biochemical Biophysical Research Communications* 1993, 193, 268–276). The receptor is found almost exclusively in the central nervous system (CNS) areas both in rat and in human. In situ hybridization studies of the 5-HT6 receptor in rat brain using mRNA indicate principal localization in the areas of 5-HT projection including striatum, nucleus accumbens, olfactory tubercle, and hippocampal formation (Ward, R. P.; Hamblin, M. W.; Lachowicz, J. E.; Hoffman, B. J.; Sibley, D. R.; Dorsa, D. M. *Neuroscience* 1995, 64,1105–1111).

There are many potential therapeutic uses for 5-HT6 ligands in humans based on direct effects and on indications from available scientific studies. These studies include the localization of the receptor, the affinity of ligands with known in vivo activity, and various animal studies conducted so far.

One potential therapeutic use of modulators of 5-HT6 receptor function is in the enhancement of cognition and memory in human diseases such as Alzheimer's.

The high levels of receptor found in important structures in the forebrain, including the caudate/putamen, hippocampus, nucleus accumbens, and cortex suggest a role for the receptor in memory and cognition since these areas are known to play a vital role in memory (Gerard, C.; Martres, M.-P.; Lefevre, K.; Miquel, M. C.; Verge, D.; Lanfumey, R.; Doucet, E.; Hamon, M.; E I Mestikawy, S. *Brain Research,* 1997, 746, 207–219). The ability of known 5-HT6 receptor ligands to enhance cholinergic transmission also supports the potential cognition use (Bentley, J. C.; Boursson, A.; Boess, F. G.; Kone, F. C.; Marsden, C. A.; Petit, N.; Sleight, A. J. *British Journal of Pharmacology,* 1999, 126(7), 1537–1542). Studies have found that a known 5-HT6 selective antagonist significantly increased glutamate and aspartate levels in the frontal cortex without elevating levels of noradrenaline, dopamine, or 5-HT. This selective elevation of neurochemicals known to be involved in memory and cognition strongly suggests a role for 5-HT6 ligands in cognition (Dawson, L. A.; Nguyen, H. Q.; Li, P. *British Journal of Pharmacology,* 2000, 130(1), 23–26). Animal studies of memory and learning with a known selective 5-HT6 antagonist found some positive effects (Rogers, D. C.; Hatcher, P. D.; Hagan, J. J. *Society of Neuroscience, Abstracts* 2000, 26, 680).

A related potential therapeutic use for 5-HT6 ligands is the treatment of attention deficit disorders (ADD, also known as Attention Deficit Hyperactivity Disorder or ADHD) in both children and adults. Because 5-HT6 antagonists appear to enhance the activity of the nigrostriatal dopamine pathway and because ADHD has been linked to abnormalities in the caudate (Ernst, M; Zametkin, A. J.; Matochik, J. H.; Jons, P. A.; Cohen, R. M. *Journal of Neuroscience* 1998, 18(15), 5901–5907), 5-HT6 antagonists may attenuate attention deficit disorders.

Early studies examining the affinity of various CNS ligands with known therapeutic utility or a strong structural resemblance to known drugs suggests a role for 5-HT6 ligands in the treatment of schizophrenia and depression. For example, clozapine (an effective clinical antipsychotic) has high affinity for the 5-HT6 receptor subtype. Also, several clinical antidepressants have high affinity for the receptor as well and act as antagonists at this site (Branchek, T. A.; Blackburn, T. P. *Annual Reviews in Pharmacology and Toxicology* 2000, 40, 319–334).

Further, recent in vivo studies in rats indicate 5-HT6 modulators may be useful in the treatment of movement disorders including epilepsy (Stean, T.; Routledge, C.; Upton, N. *British Journal of Pharmacology* 1999, 127 Proc. Supplement 131 P and Routledge, C.; Bromidge, S. M.; Moss, S. F.; Price, G. W.; Hirst, W.; Newman, H.; Riley, G.; Gager, T.; Stean, T.; Upton, N.; Clarke, S. E.; Brown, A. M. *British Journal of Pharmacology* 2000, 130(7), 1606–1612).

Taken together, the above studies strongly suggest that compounds which are 5-HT6 receptor ligands may be useful for therapeutic indications including: the treatment of diseases associated with a deficit in memory, cognition, and learning such as Alzheimer's and attention deficit disorder; the treatment of personality disorders such as schizophrenia; the treatment of behavioral disorders, e.g., anxiety, depression and obsessive compulsive disorders; the treatment of motion or motor disorders such as Parkinson's disease and epilepsy; the treatment of diseases associated with neurodegeneration such as stroke and head trauma; or withdrawal from drug addiction including addiction to nicotine, alcohol, and other substances of abuse.

Therefore, it is an object of this invention to provide compounds which are useful as therapeutic agents in the treatment of a variety of central nervous system disorders related to or affected by the 5-HT6 receptor.

It is another object of this invention to provide therapeutic methods and pharmaceutical compositions useful for the treatment of central nervous system disorders related to or affected by the 5-HT6 receptor.

It is a feature of this invention that the compounds provided may also be used to further study and elucidate the 5-HT6 receptor.

These and other objects and features of the invention will become more apparent by the detailed description set forth hereinbelow.

SUMMARY OF THE INVENTION

The present invention provides a 1-(aminoalkyl)-3-sulfonylazaindole derivative of formula I

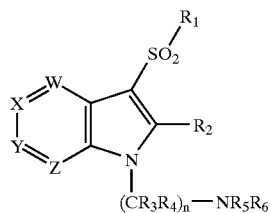

wherein
W is N or $CR_7$;
X is N or $CR_8$;
Y is N or $CR_9$;
Z is N or $CR_{10}$ with the proviso that at least one and no more than two of W, X, Y and Z must be N;
n is an integer of 2, 3, 4 or 5;
$R_1$ is an optionally substituted $C_1$–$C_6$alkyl, $C_3$–$C_7$cycloalkyl, aryl, or heteroaryl group or an optionally substituted 8- to 13-membered bicyclic or tricyclic ring system having a N atom at the bridgehead and optionally containing 1, 2 or 3 additional heteroatoms selected from N, O or S;
$R_2$ is H, halogen, or a $C_1$–$C_6$alkyl, $C_1$–$C_6$alkoxy, $C_3$–$C_7$cycloalkyl, aryl or heteroaryl group each optionally substituted;
$R_3$ and $R_4$ are each independently H or an optionally substituted $C_1$–$C_6$alkyl group;
$R_5$ and $R_6$ are each independently H or a $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl group each optionally substituted, or $R_5$ and $R_6$ may be taken together with the atom to which they are attached to form an optionally substituted 5- to 8-membered ring optionally containing an additional heteroatom selected from O, $NR_{11}$ or $SO_m$;
$R_7$, $R_8$, $R_9$ and $R_{10}$ are independently H, halogen, CN, $OCO_2R_{12}$, $CO_2R_{13}$, $CONR_{14}R_{15}$, $SO_pR_{16}$, $NR_{17}R_{18}$, $OR_{19}$, $COR_{20}$, or a $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl group each optionally substituted;
$R_{11}$, $R_{12}$, $R_{13}$, $R_{16}$, $R_{19}$ and $R_{20}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;
$R_{14}$ and $R_{15}$ are each independently H or an optionally substituted $C_1$–$C_6$alkyl group or $R_{14}$ and $R_{15}$ may be taken together with the atom to which they are attached to form a 5- to 7-membered ring optionally containing another heteroatom selected from O, $NR_{22}$ or S;
$R_{17}$ and $R_{18}$ are each independently H or an optionally substituted $C_1$–$C_4$alkyl group or $R_{17}$ and $R_{18}$ may be taken together with the atom to which they are attached to form a 5- to 7-membered ring optionally containing another heteroatom selected from O, $NR_{21}$ or $SO_x$;
$R_{21}$ and $R_{22}$ are each independently H or a $C_1$–$C_6$alkyl, $C_2$–$C_6$alkenyl, $C_3$–$C_7$cycloalkyl, cycloheteroalkyl, aryl or heteroaryl group each optionally substituted; and
m, p and x are each independently 0 or an integer of 1 or 2; or a stereoisomer thereof or a pharmaceutically acceptable salt thereof.

The present invention also provides methods and compositions useful for the therapeutic treatment of central nervous system disorders related to or affected by the 5-HT6 receptor.

DETAILED DESCRIPTION OF THE INVENTION

The 5-hydroxytryptamine-6 (5-HT6) receptor is one of the most recent receptors to be identified by molecular cloning. Its ability to bind a wide range of therapeutic compounds used in psychiatry, coupled with its intriguing distribution in the brain has stimulated significant interest in new compounds which are capable of interacting with or affecting said receptor. Significant efforts are being made to understand the possible role of the 5-HT6 receptor in psychiatry, cognitive dysfunction, motor function and control, memory, mood and the like. To that end, compounds which demonstrate a binding affinity for the 5-HT6 receptor are earnestly sought both as an aid in the study of the 5-HT6 receptor and as potential therapeutic agents in the treatment of central nervous system disorders, for example see C. Reavill and D. C. Rogers, Current Opinion in Investigational Drugs, 2001, 2(1):104–109, Pharma Press Ltd.

Surprisingly, it has now been found that 1-(aminoalkyl)-3-sulfonylazaindole derivatives of formula I demonstrate 5-HT6 affinity. Advantageously, said azaindole derivatives may be used as effective therapeutic agents for the treatment of central nervous system (CNS) disorders associated with or affected by the 5-HT6 receptor. Accordingly, the present invention provides 1-(aminoalkyl)-3-sulfonylazaindole derivatives of formula I

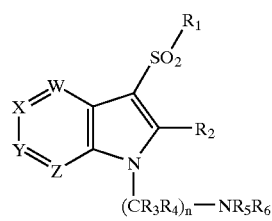

wherein
W is N or $CR_7$;
X is N or $CR_8$;
Y is N or $CR_9$;
Z is N or $CR_{10}$ with the proviso that at least one and no more than two of W, X, Y and Z must be N;
n is an integer of 2, 3, 4 or 5;
$R_1$ is an optionally substituted $C_1$–$C_6$alkyl, $C_3$–$C_7$cycloalkyl, aryl, or heteroaryl group or an optionally substituted 8- to 13-membered bicyclic or tricyclic ring system having a N atom at the bridgehead and optionally containing 1, 2 or 3 additional heteroatoms selected from N, O or S;
$R_2$ is H, halogen, or a $C_1$–$C_6$alkyl, $C_1$–$C_6$alkoxy, $C_3$–$C_7$cycloalkyl, aryl or heteroaryl group each optionally substituted;
$R_3$ and $R_4$ are each independently H or an optionally substituted $C_1$–$C_6$alkyl group;
$R_5$ and $R_6$ are each independently H or a $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl group each optionally substituted, or $R_5$ and $R_6$ may be taken together with the atom to which they are attached to form an optionally substituted 5- to 8-membered ring optionally containing an additional heteroatom selected from O, $NR_{11}$ or $SO_m$;
$R_7$, $R_8$, $R_9$ and $R_{10}$ are independently H, halogen, CN, $OCO_2R_{12}$, $CO_2R_{13}$, $CONR_{14}R_{15}$, $SO_pR_{16}$, $NR_{17}R_{18}$, OR$_{19}$, COR$_{20}$, or a C$_1$–C$_6$alkyl, C$_2$–C$_6$alkenyl, C$_2$–C$_6$alkynyl, C$_3$–C$_7$cycloalkyl, cycloheteroalkyl, aryl or heteroaryl group each optionally substituted;

R$_{11}$, R$_{12}$, R$_{13}$, R$_{16}$, R$_{19}$ and R$_{20}$ are each independently H or a C$_1$–C$_6$alkyl, C$_2$–C$_6$alkenyl, C$_2$–C$_6$alkynyl, C$_3$–C$_6$cycloalkyl, cycloheteroalkyl, aryl or heteroaryl group each optionally substituted;

R$_{14}$ and R$_{15}$ are each independently H or an optionally substituted C$_1$–C$_6$alkyl group or R$_{14}$ and R$_{15}$ may be taken together with the atom to which they are attached to form a 5- to 7-membered ring optionally containing another heteroatom selected from O, NR$_{22}$ or S;

R$_{17}$ and R$_{18}$ are each independently H or an optionally substituted C$_1$–C$_4$alkyl group or R$_{17}$ and R$_{18}$ may be taken together with the atom to which they are attached to form a 5- to 7-membered ring optionally containing another heteroatom selected from O, NR$_{21}$ or SO$_x$;

R$_{21}$ and R$_{22}$ are each independently H or a C$_1$–C$_6$alkyl, C$_2$–C$_6$alkenyl, C$_3$–C$_7$cycloalkyl, cycloheteroalkyl, aryl or heteroaryl group each optionally substituted; and m, p and x are each independently 0 or an integer of 1 or 2; or a stereoisomer thereof or a pharmaceutically acceptable salt thereof.

As used in the specification and claims, the term halogen designates F, Cl, Br or I and the term cycloheteroalkyl designates a 5- to 7-membered cycloalkyl ring system containing 1 or 2 heteroatoms, which may be the same or different, selected from N, O or S and optionally containing one double bond. Exemplary of the cycloheteroalkyl ring systems included in the term as designated herein are the following rings wherein X$_1$ is NR, O or S; and R is H or an optional substituent as described hereinbelow:

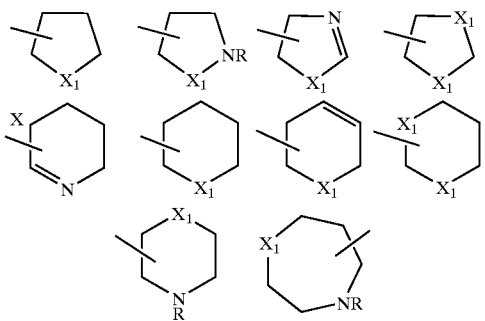

Similarly, as used in the specification and claims, the term heteroaryl designates a 5- to 10-membered aromatic ring system containing 1, 2 or 3 heteroatoms, which may be the same or different, selected from N, O or S. Such heteroaryl ring systems include pyrrolyl, azolyl, oxazolyl, thiazolyl, imidazolyl, furyl, thienyl, quinolinyl, isoquinolinyl, indolinyl, benzothienyl, benzofuranyl, benzisoxazolyl or the like. The term aryl designates a carbocyclic aromatic ring system e.g., having 6 to 14 carbon atoms such as phenyl, naphthyl, anthracenyl or the like. The term haloalkyl as used herein designates a C$_n$H$_{2n+1}$ group having from one to 2n+1 halogen atoms which may be the same or different and the term haloalkoxy as used herein designates an OC$_n$H$_{2n+1}$ group having from one to 2n+1 halogen atoms which may be the same or different.

Exemplary of the 8- to 13-membered bicyclic or tricyclic ring systems having a N atom at the bridgehead and optionally containing 1, 2 or 3 additional heteroatoms selected from N, O or S included in the term as designated herein are the following ring systems wherein W$_2$ is NR, O or S; and R is H or an optional substituent as described hereinbelow:

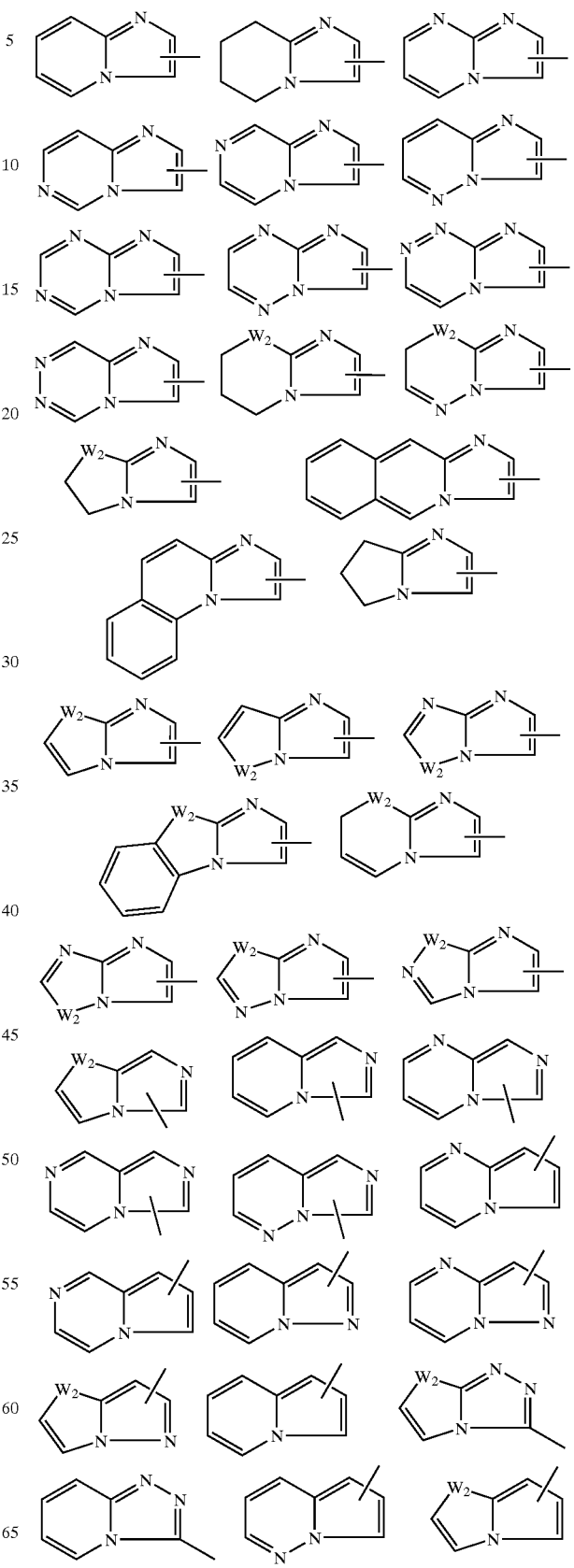

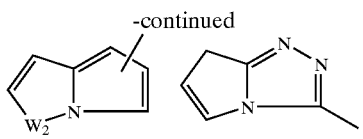

In the specification and claims, when the terms $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl are designated as being optionally substituted, the substituent groups which are optionally present may include halogen atoms, nitro, cyano, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, heterocyclyl (such as heteroaryl or cycloheteroalkyl) or cycloalkyl groups, preferably halogen atoms or lower (e.g. $C_1$–$C_6$)alkyl groups. Typically, 0–3 substituents may be present. When any of the foregoing substituents represents or contains an alkyl substituent group, this may be linear or branched and may contain up to 12, preferably up to 6, more preferably up to 4 carbon atoms.

Pharmaceutically acceptable salts may be any acid addition salt formed by a compound of formula I and a pharmaceutically acceptable acid such as phosphoric, sulfuric, hydrochloric, hydrobromic, citric, maleic, malonic, mandelic, succinic, fumaric, acetic, lactic, nitric, sulfonic, p-toluene sulfonic, methane sulfonic acid or the like.

Compounds of the invention include esters, carbamates or other conventional prodrug forms, which in general, are functional derivatives of the compounds of the invention and which are readily converted to the inventive active moiety in vivo. Correspondingly, the method of the invention embraces the treatment of the various conditions described hereinabove with a compound of formula I or with a compound which is not specifically disclosed but which, upon administration, converts to a compound of formula I in vivo. Also included are metabolites of the compounds of the present invention defined as active species produced upon introduction of these compounds into a biological system.

Compounds of the invention may exist as one or more stereoisomers. The various stereoisomers include enantiomers, diastereomers, atropisomers and geometric isomers. One skilled in the art will appreciate that one stereoisomer may be more active or may exhibit beneficial effects when enriched relative to the other stereoisomer(s) or when separated from the other stereoisomer(s). Additionally, the skilled artisan knows how to separate, enrich or selectively prepare said stereoisomers. Accordingly, the present invention comprises compounds of Formula I, the stereoisomers thereof and the pharmaceutically acceptable salts thereof. The compounds of the invention may be present as a mixture of stereoisomers, individual stereoisomers, or as an optically active or enantiomerically pure form.

Preferred compounds of the invention are those compounds of formula I wherein W or Z is N. Also preferred are those compounds of formula I wherein n is 2. Another group of preferred compounds of formula I are those compounds wherein $R_1$ is an optionally substituted phenyl, naphthyl or imidazothiazolyl group.

More preferred compounds of the invention are those formula I compounds wherein W is $CR_7$; X is $CR_8$; Y is $CR_9$; and Z is N. Another group of more preferred compounds are those formula I compounds wherein W is N; X is $CR_8$; Y is $CR_9$; and Z is $CR_{10}$. More preferred compounds of formula I also include those compounds wherein n is 2 and $R_3$ and $R_4$ are H. Further, more preferred compounds are those formula I compounds wherein W or Z is N; n is 2; $R_1$ is an optionally substituted phenyl, naphthyl or imidazothiazolyl group; $R_2$, $R_3$ and $R_4$ are H; and $R_5$ and $R_6$ are each independently H or $C_1$–$C_3$alkyl.

Examples of preferred compounds of the invention include:

2-[3-(phenylsulfonyl)-1H-pyrrolo[2,3-b]pyridin-1-yl]ethylamine;
2-[3-(phenylsulfonyl)-1H-pyrrolo[2,3-c]pyridin-1-yl]ethylamine;
2-[3-(phenylsulfonyl)-1H-pyrrolo[3,2-c]pyridin-1-yl]ethylamine;
2-{3-[(4-fluorophenyl)sulfonyl]-1H-pyrrolo[3,2-b]pyridin-1-yl}ethylamine;
2-{3-[(4-methylphenyl)sulfonyl]-1H-pyrrolo[2,3-b]pyridin-1-yl}ethylamine;
2-[3-(naphth-1-yl)sulfonyl)-1H-pyrrolo[2,3-b]pyridin-1-yl]ethylamine;
2-{3-[(6-chloro-imidazo[2,1-b][1,3]thiazol-5-yl)sulfonyl]-1H-pyrrolo[2,3-b]pyridin-1-yl}ethylamine;
2-{3-[(3-chlorophenyl)sulfonyl]-1H-pyrrolo[2,3-b]pyridin-1-yl}ethylamine;
2-{3-[(2-chlorophenyl)sulfonyl]-1H-pyrrolo[2,3-c]pyridin-1-yl}ethylamine;
2-{3-[(3-methoxyphenyl)sulfonyl]-1H-pyrrolo[3,2-c]pyridin-1-yl}ethylamine;
2-{3-[(4-fluorophenyl)sulfonyl]-1H-pyrrolo[3,2-b]pyridin-1-yl}ethylamine;
N,N-dimethyl-N-(2-{3-[(3-fluorophenyl)sulfonyl]-1H-pyrrolo[2,3-b]pyridin-1-yl}ethyl)amine;
N,N-dimethyl-N-{2-[3-(naphth-1-ylsulfonyl)-1H-pyrrolo[2,3-b]pyridin-1-yl]ethyl}amine;
N,N-dimethyl-N-(2-{3-[(6-chloroimidazo[1,2-b][1,3]thiazol-5-yl)sulfonyl]-1H-pyrrolo[2,3-b]pyridin-1-yl}ethyl)amine;
N,N-dimethyl-N-(2-{3-[(3-chlorophenyl)sulfonyl]-1H-pyrrolo[2,3-b]pyridine-1-yl}ethyl)amine;
3-[3-(phenylsulfonyl)-1H-pyrrolo[2,3-b]pyridin-1-yl]propan-1-amine;
3-[3-(phenylsulfonyl)-1H-pyrrolo[2,3-c]pyridin-1-yl]propan-1-amine;
3-[3-(phenylsulfonyl)-1H-pyrrolo[3,2-c]pyridin-1-yl]propan-1-amine;
3-{3-[(4-fluorophenyl)sulfonyl]-1H-pyrrolo[3,2-b]pyridin-1-yl}propan-1-amine;
2-{6-chloro-3-[(3-chlorophenyl)sulfonyl]-1H-pyrrolo[2,3-b]pyridin-1-yl}ethylamine;
2-{7-chloro-3-[(2-chlorophenyl)sulfonyl]-1H-pyrrolo[2,3-c]pyridin-1-yl}ethylamine;
4-{3-[(3-methoxyphenyl)sulfonyl]-1H-pyrrolo[3,2-c]pyridin-1-yl}butan-1-amine;
4-{3-[(4-fluorophenyl)sulfonyl]-1H-pyrrolo[3,2-b]pyridin-1-yl}butan-1-amine;
N,N-dimethyl-N-{2-[3-(phenylsulfonyl)-1H-pyrrolo[2,3-c]pyridin-1-yl]ethyl}amine;
N,N-dimethyl-N-{2-[3-(phenylsulfonyl)-1H-pyrrolo[3,2-c]pyridin-1-yl]ethyl}amine;
N,N-dimethyl-N-{2-[3-(thien-2-yl)-1H-pyrrolo[2,3-b]pyridin-1-yl]ethyl}amine;
N,N-dimethyl-N-{2-[3-(naphth-1-yl)-1H-pyrrolo[2,3-b]pyridin-1-yl]ethyl}amine;
N,N-dimethyl-N-(2-{3-[(4-fluorophenyl)sulfonyl]-1H-pyrrolo[3,2-b]pyridin-1-yl}ethyl)amine;
N-methyl-N-(2-{3-[(3-chlorophenyl)sulfonyl]-1H-pyrrolo[2,3-b]pyridin-1-yl}ethyl)amine;
N-methyl-N-(2-{3-[(3-fluorophenyl)sulfonyl]-1H-pyrrolo[2,3-b]pyridin-1-yl}ethyl)amine;
N-methyl-N-{2-[3-(naphth-1-ylsulfonyl)-1H-pyrrolo[2,3-b]pyridin-1-yl]ethyl}amine;

N-methyl-N-(2-{3-[(6-chloroimidazo[1,2-b][1,3]thiazol-5-yl)sulfonyl]-1H-pyrrolo[2,3-b]pyridin-1-yl}ethyl)amine;
N-methyl-N-(2-{3-[(2-chlorophenyl)sulfonyl]-1H-pyrrolo[2,3-c]pyridin-1-yl}ethyl)amine;
N-methyl-N-(2-{3-[(3-methoxyphenyl)sulfonyl]-1H-pyrrolo[3,2-c]pyridin-1-yl}ethyl)amine;
N-benzyl-N-(2-{3-[(4-fluorophenyl)sulfonyl]-1H-pyrrolo[3,2-b]pyridin-1-yl}ethyl)amine;
N,N-dibenzyl-3-[3-(phenylsulfonyl)-1H-pyrrolo[2,3-b]pyridin-1-yl]propan-1-amine;
3-[3-(phenylsulfonyl)-1H-pyrrolo[2,3-c]pyridin-1-yl]propan-1-amine;
3-[3-(phenylsulfonyl)-1H-pyrrolo[3,2-c]pyridin-1-yl]propan-1-amine;

the stereoisomers thereof or the pharmaceutically acceptable salts thereof.

Advantageously, the present invention provides a process for the preparation of a compound of formula I which comprises reacting a compound of formula II with a haloalkylamine of formula III in the presence of a base optionally in the presence of a solvent. The process of the invention is shown in flow diagram I wherein Hal represents Cl, Br or I.

Flow Diagram I

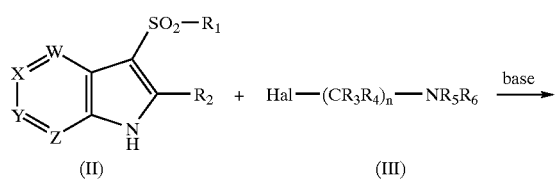

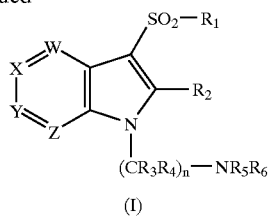

Bases suitable for use in the process of the invention include strong bases such as NaH, KOt-Bu, NaOH or any conventional base capable of removing a proton from a basic azaindole nitrogen atom.

Solvents suitable for use in the process of the invention include polar solvents such as dimethyl formamide, dimethyl sulfoxide, acetonitrile, tetrahydrofuran, or the like. If two immiscible solvents are used, a phase transfer catalyst may be present. Preferably, for the preparation of those compounds of formula I wherein $R_5$ and $R_6$ are H, the compound of formula II may be reacted with a base as described hereinabove in the presence of a phase transfer catalyst, such as tetrabutylammonium hydrogensulfate, to give the desired compound of formula I wherein $R_5$ and $R_6$ are H.

Alternatively, compounds of formula I wherein $R_5$ and $R_6$ are H (Ia) may be prepared by reacting the formula II compound with a di-haloalkyl compound of formula IV to give the 1-(haloalkyl)azaindole of formula V; reacting the formula V azaindole with potassium phthalimide to give the intermediate of formula VI and reacting said intermediate with hydrazine to give the desired formula Ia compound. The reaction sequence is shown in flow diagram II wherein Hal represents Cl, Br or I.

Flow Diagram II

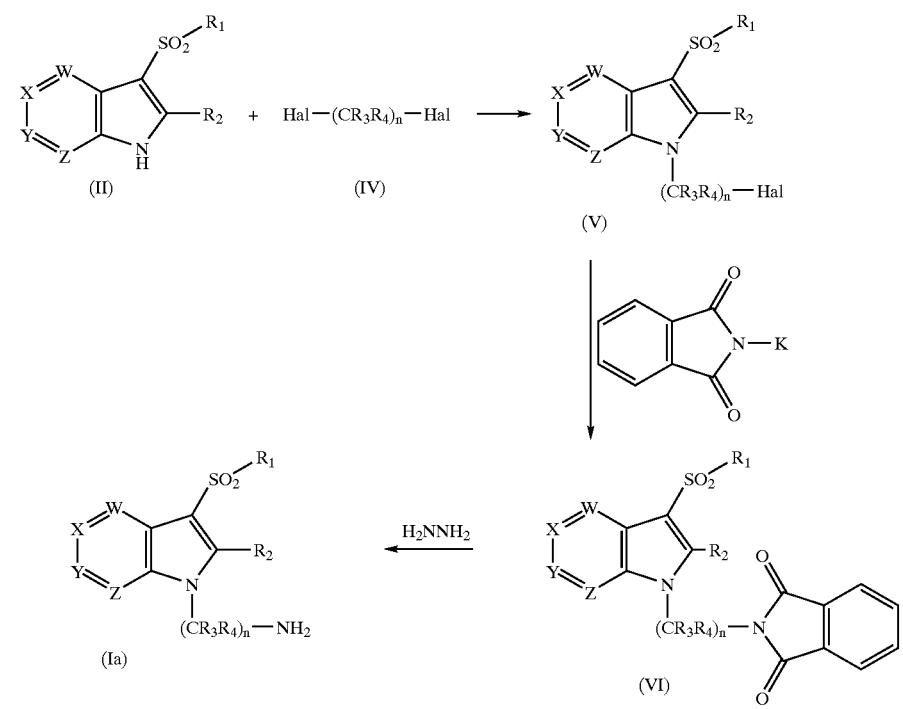

Compounds of formula V may also be reacted directly with an amine, $HNR_5R_6$, to give compounds of formula I. Compounds of formula II may be prepared using conventional synthetic methods and, if required, standard separation and isolation techniques. For example, a nitropyridine compound of formula VII may be reacted with a chloromethylsulfonyl compound of formula VIII in the presence of a strong base to give the intermediate of formula IX; said formula IX intermediate may then be treated with a reducing agent such as Fe, Zn or Sn in the presence of an acid to give the amine of formula X; said amine may then be acylated with the appropriate orthoester of formula XI to give the formula XII compound; and said compound may be cyclized in the presence of a base to give the desired formula II 3-sulfonyl azaindole. The general synthetic method is described by W. Wojciechowski and M. Makosza, *Synthesis* 1986, 651–653. The reaction sequence is shown in flow diagram III.

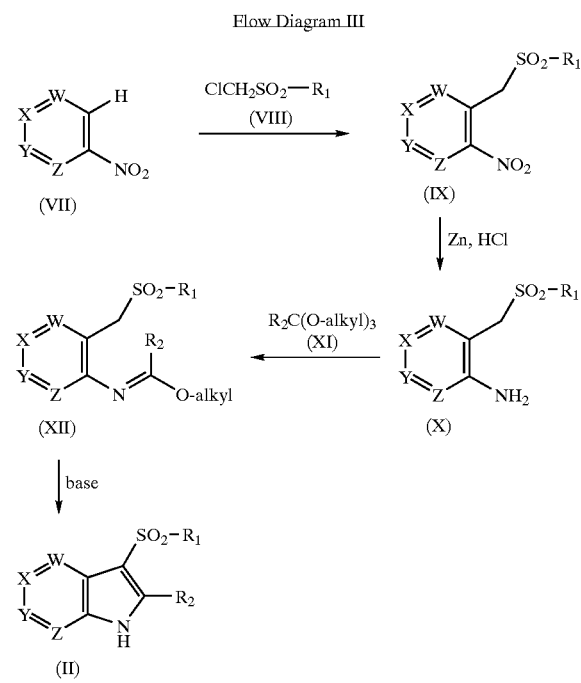

Compounds of formula II may also be prepared directly from an azaindole compound, i.e. an azaindole of formula XIII may be reacted with iodine, optionally in the presence of KI, to give the corresponding 3-iodoazaindole of formula XIV and said 3-iodoazaindole may be coupled with an appropriate thiol of formula XV to give the 3-thioazaindole of formula XVI. Said formula XVI compound may then be oxidized using conventional oxidizing reagents such as $H_2O_2$, m-chloroperbenzoic acid or the like to afford the formula II intermediate. The reaction is shown in flow diagram IV.

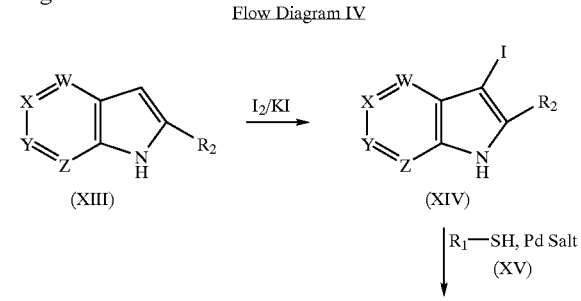

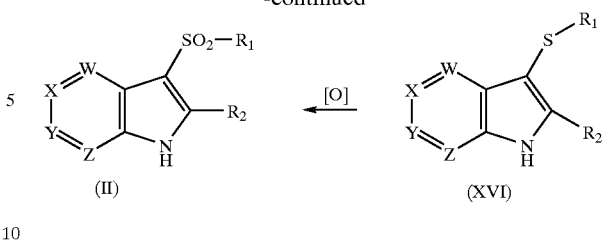

Alternatively, the formula XVI 3-thioazaindole intermediate may be prepared in a single step from the azaindole of formula XIII by reacting said formula XIII compound with the formula XV thiol in the presence of iodine, preferably in a polar solvent such as aqueous alcohol. The thus-obtained formula II compounds may then be carried on to the desired compounds of formula I by alkylation of the basic azaindole nitrogen as shown in flow diagrams I and II hereinabove.

Compounds of formula XIII may also be converted to the desired compounds of formula I wherein $R_5$ and $R_6$ are other than H (Ia) by reacting the formula XIII azaindole with an amine of formula IIIa wherein $R_5$ and $R_6$ are other than H to give the N-alkylated compound of formula XVII; reacting the formula XVII compound with a sulfonyl chloride of formula XVIII, optionally in the presence of a reagent such as $Ag(OSO_2CF_3)$ or $Bi(OSO_2CF_3)_3$, to give the desired compound of formula Ia. Similarly, compounds of formula I wherein $R_5$ and $R_6$ are H (Ib) may be prepared directly from the formula XIII intermediate by reacting said formula XIII intermediate with a nitrile of formula XIX to give the corresponding alkylated compound of formula XX; sulfonylating said formula XX compound to give the compound of formula XXI; and reducing the formula XXI compound using conventional reducing reagents such as borane in tetrahydrofuran (THF) to give the desired compounds of formula Ib. The reactions are shown in flow diagram V wherein Hal represents Cl, Br or I.

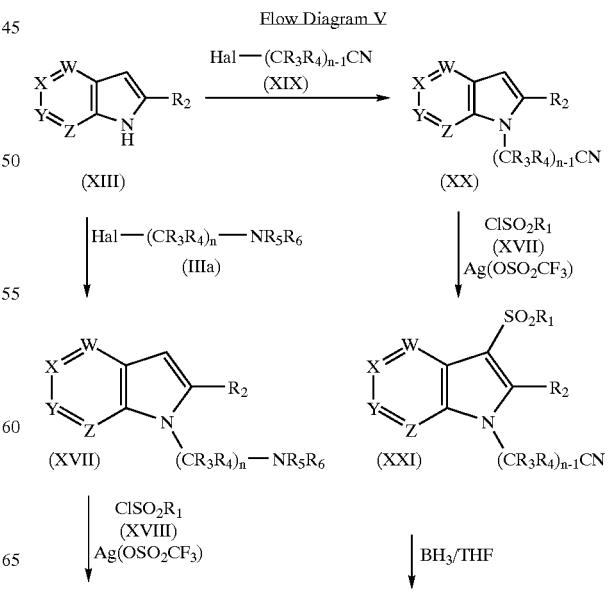

-continued

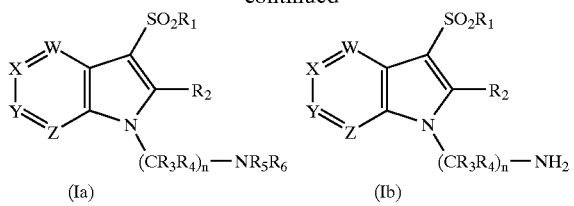

(Ia)          (Ib)

Advantageously, the formula I compounds of the invention are useful for the treatment of CNS disorders relating or or affected by 5-HT6 receptor including motor, mood, personality, behavioral, psychiatric, cognitive, neurodegenerative, or the like disorders, for example Alzheimer's disease, Parkinson's disease, attention deficit disorder, anxiety, epilepsy, depression, obsessive compulsive disorder, sleep disorders, neurodegenerative disorders (such as head trauma or stroke), feeding disorders (such as anorexia or bulimia), schizophrenia, memory loss, disorders associated with withdrawal from drug or nicotine abuse, or the like or certain gastrointestinal disorders such as irritable bowel syndrome. Accordingly, the present invention provides a method for the treatment of a disorder of the central nervous system related to or affected by the 5-HT6 receptor in a patient in need thereof which comprises providing said patient a therapeutically effective amount of a compound of formula I as described hereinabove. The compounds may be provided by oral or parenteral administration or in any common manner known to be an effective administration of a therapeutic agent to a patient in need thereof.

The term "providing" as used herein with respect to providing a compound or substance embraced by the invention, designates either directly administering such a compound or substance, or administering a prodrug, derivative or analog which forms an equivalent amount of the compound or substance within the body.

The therapeutically effective amount provided in the treatment of a specific CNS disorder may vary according to the specific condition(s) being treated, the size, age and response pattern of the patient, the severity of the disorder, the judgment of the attending physician and the like. In general, effective amounts for daily oral administration may be about 0.01 to 1,000 mg/kg, preferably about 0.5 to 500 mg/kg and effective amounts for parenteral administration may be about 0.1 to 100 mg/kg, preferably about 0.5 to 50 mg/kg.

In actual practice, the compounds of the invention are provided by administering the compound or a precursor thereof in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula I as described hereinabove.

Solid carriers suitable for use in the composition of the invention include one or more substances which may also act as flavoring agents, lubricants, solubilizers, suspending agents, fillers, glidants, compression aides, binders, tablet-disintegrating agents or encapsulating materials. In powders, the carrier may be a finely divided solid which is in admixture with a finely divided compound of formula I. In tablets, the formula I compound may be mixed with a carrier having the necessary compression properties in suitable proportions and compacted in the shape and size desired.

Said powders and tablets may contain up to 99% by weight of the formula I compound. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Any pharmaceutically acceptable liquid carrier suitable for preparing solutions, suspensions, emulsions, syrups and elixirs may be employed in the composition of the invention. Compounds of formula I may be dissolved or suspended in a pharmaceutically acceptable liquid carrier such as water, an organic solvent, or a pharmaceutically acceptable oil or fat, or a mixture thereof. Said liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

Compositions of the invention which are sterile solutions or suspensions are suitable for intramuscular, intraperitoneal or subcutaneous injection. Sterile solutions may also be administered intravenously. Inventive compositions suitable for oral administration may be in either liquid or solid composition form.

For a more clear understanding, and in order to illustrate the invention more clearly, specific examples thereof are set forth hereinbelow. The following examples are merely illustrative and are not to be understood as limiting the scope and underlying principles of the invention in any way.

The term HNMR designates proton nuclear magnetic resonance. The terms EtOAc and DMF designate ethyl acetate and dimethyl formamide, respectively. The term DMSO designates dimethylsulfoxide. All chromatography is performed using $SiO_2$ as support.

EXAMPLE 1

Preparation of 3-(Phenylthio)-1H-pyrrolo[2,3-b]pyridine

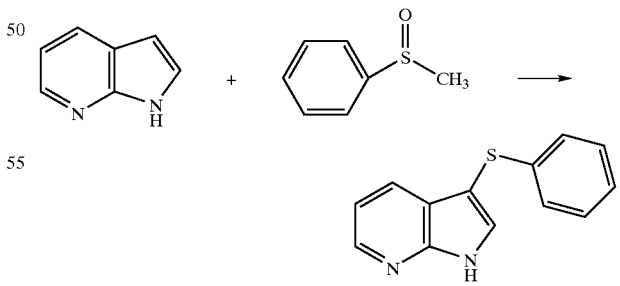

A solution of methyl phenyl sulfoxide (8.33 g, 59.4 mmol) in $CH_2Cl_2$ is chilled to −78° C. and treated dropwise with trifluoroacetic anhydride (4.1 mL, 5.3 mmol). After stirring for 30 min at −78° C., a solution of 7-azaindole (5.2 g, 44.0 mmol) in $CH_2Cl_2$ is added. After 30 min at −78° C., triethylamine (74 mL, 534 mmol) is added and the reaction is allowed to reach ambient temperature. After stirring for 3.5 days, the reaction is concentrated in vacuo, treated with saturated aqueous NaHCO₃ and extracted with CH₂Cl₂. The organic extracts are combined and concentrated in vacuo. The resultant residue is crystallized from methanol/H₂O and recrystallized from CH₂Cl₂/hexane to afford the title compound as an off-white solid, 1.26 g, mp 188–189° C., characterized by mass spectral analyses and HNMR analyses.

EXAMPLE 2

Preparation of 3-(Phenylsulfonyl)-1H-pyrrolo[2,3-b]pyridine

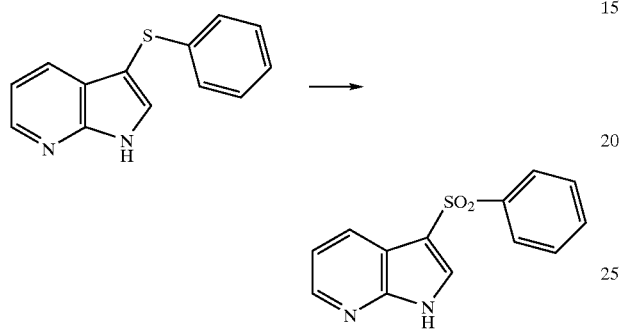

A solution of 3-(phenylthio)-1H-pyrrolo[2,3-b]pyridine (100 mg, 0.44 mmol) in t-butyl alcohol is treated with MnSO₄.H₂O (4 mg, 0.020 mmol) and cooled to 0° C. A mixture of 30% aqueous hydrogen peroxide (500 mg, 4.41 mmol) and 0.2 N aqueous NaHCO₃ (7.5 mL) is added dropwise. The reaction is stirred for 23 h at 20° C., diluted with saturated aqueous NaHCO₃ and extracted with ethyl acetate. The combined extracts are dried over MgSO₄ and concentrated in vacuo. Chromatography (1:50 methanol:CH₂Cl₂) of the resultant residue yields a solid product which is recrystallized from CH₂Cl₂/hexane to afford the title compound as a pinkish-white solid, 58 mg, mp>250° C., characterized by mass spectral and HNMR analyses.

EXAMPLE 3

Preparation of 1-(2-Chloroethyl)-3-(phenylsulfonyl)-1H-pyrrolo[2,3b]pyridine

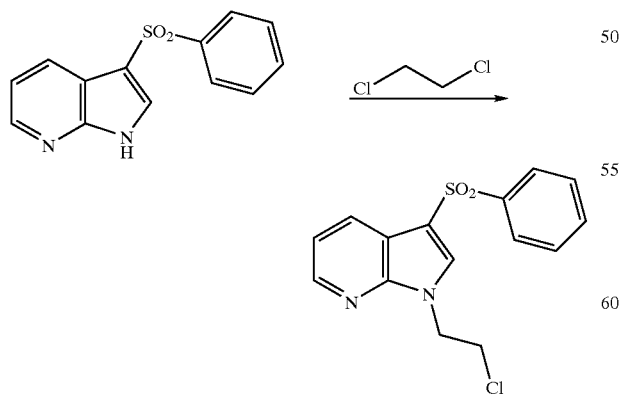

A solution of 3-(phenylsulfonyl)-1H-pyrrolo[2,3-b]pyridine (4.30 g, 16.6 mmol) in 1,2-dichloroethane (33 mL, 420 mmol) is treated with Aliquat®[1] (6.9 g) and 50% aqueous NaOH (1.6 g, 20 mmol). The reaction is stirred for 6 h at 45° C. The cooled solution is diluted with H₂O (200 mL) and extracted with CH₂Cl₂ (3×250 mL). The combined CH₂Cl₂ extracts are dried over MgSO₄ and concentrated in vacuo to a brown gum. This gum is chromatographed (1:4 ethyl acetate:hexanes) and then crystallized from ethyl acetate:hexanes to afford the title compound as a white solid, 3.84 g, mp 117–119° C., characterized by mass spectral and HNMR analyses.

---

[1] Tricaprylmethylammonium chloride, manufactured by Aldrich, Milwaukee, Wis.

EXAMPLE 4

Preparation of 2-{2-[3-(Phenylsulfonyl)-1H-pyrrolo[2,3-b]pyridine-1-yl]ethyl}-1H-isoindole-1,3(2H)-dione

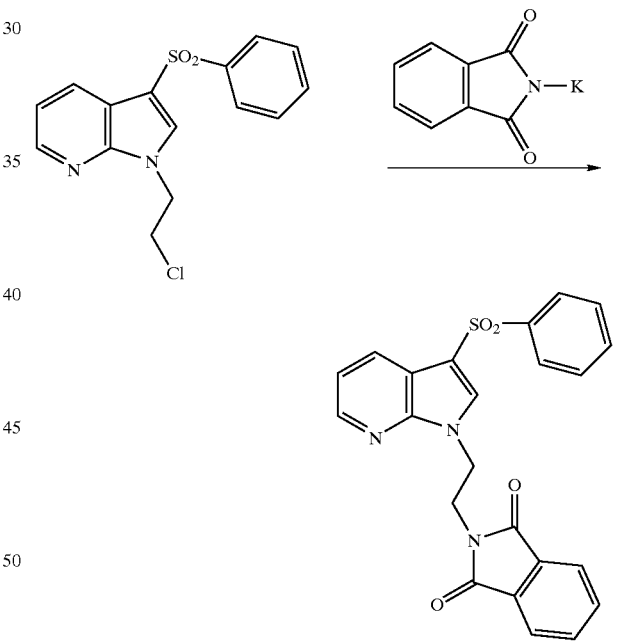

A solution of 1-(2-chloroethyl)-3-(phenylsulfonyl)-1H-pyrrolo[2,3-b]pyridine (3.84 g, 12.0 mmol) in DMF is treated with potassium phthalate (2.78 g, 15.0 mmol, heated at 115° C. for 16 h, cooled to room temperature, diluted with water and extracted with ethyl acetate. The combined extracts are washed with brine, dried over MgSO₄ and concentrated in vacuo. The resultant residue is crystallized from CH₂Cl₂/hexane to afford the title compound as a white solid, 4.54 g, characterized by HNMR analysis.

EXAMPLE 5

Preparation of 2-[3-(Phenylsulfonyl)-1H-pyrrolo[2,3-b]pyridin-1-yl]ethylamine dihydrochloride

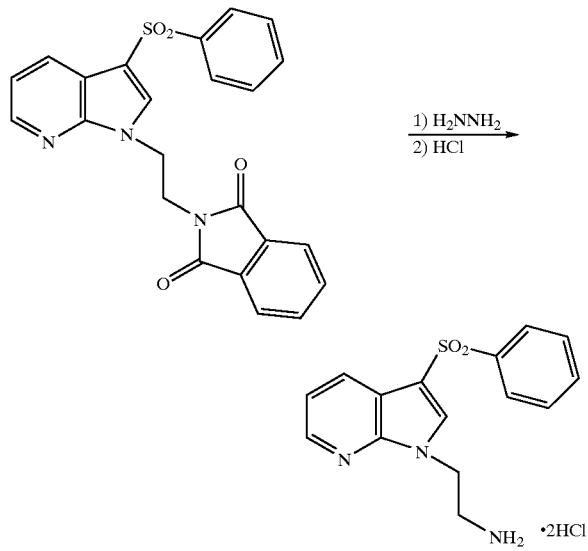

A solution of 2-{2-[3-(phenylsulfonyl)-1H-pyrrolo[2,3-b]pyridin-1-yl]ethyl}-1H-isoindole-1,3(2H)-dione (4.54 g, 10.5 mmol) in dioxane is treated with anhydrous hydrazine (8.3 mL, 265 mmol), heated at 50° C. for 3 h, concentrated in vacuo, diluted with water and extracted with $CH_2Cl_2$. The combined extracts are dried over $MgSO_4$ and concentrated in vacuo to give a clear gum residue. Chromatography (1:9 methanol:$CH_2Cl_2$) of the residue affords the free amine of the title compound as a clear gum. The free amine is dissolved in ethanol, acidified with 2N aqueous HCl and concentration in vacuo. Crystallization of the resultant residue from ethanol/ether affords the title compound as a white solid, 3.20 g, mp 195–197° C., characterized by mass spectral and HNMR analyses.

EXAMPLE 6

Preparation of N,N-Dimethyl-N-{2-[3-(phenylsulfonyl)-1H-pyrrolo[2,3-b]pyridin-1-yl]ethyl}amine dihydrochloride

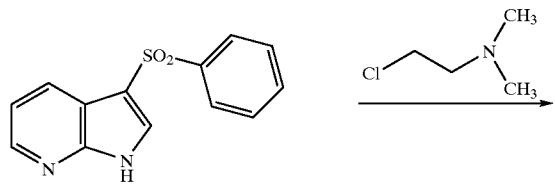

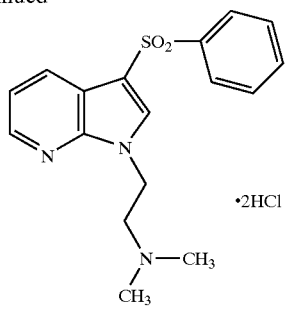

A solution of 3-(phenylsulfonyl)-1H-pyrrolo[2,3-b]pyridine (400 mg, 1.55 mmol) in dry DMF is chilled to 0° C., treated with sodium hydride (60% in oil, 97 mg, 2.43 mmol), stirred for 3 h at 20° C., cooled to −20° C., treated with 2-(dimethylamino)-ethyl chloride hydrochloride (336 mg, 2.33 mmol), stirred at 60° C. for 16 h, cooled to room temperature, quenched with water and extracted with ethyl acetate. The organic extracts are combined, washed with brine, dried over $MgSO_4$ and concentrated in vacuo to afford the free amine of the title compound as a yellowish gum. The gum is dissolved in ethanol, treated with 1N aqueous HCl and concentrated in vacuo. Crystallization of the resultant residue from ethanol/ether affords the title compound as a light tan solid, 111 mg, mp 214–217° C., characterized by mass spectral and HNMR analyses.

EXAMPLE 7

Preparation of 2-{3-[(4-Methylphenyl)sulfonyl]-1H-pyrrolo[2,3-b]pyridin-1-yl}ethylamine dihydrochloride

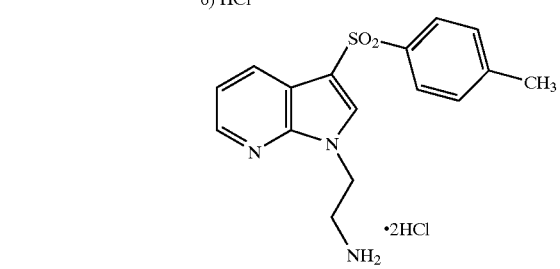

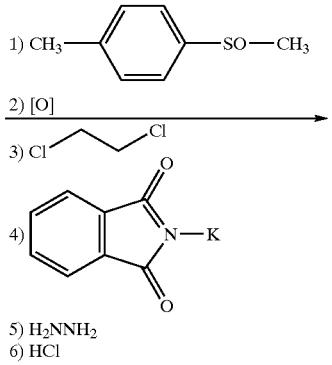

Using essentially the same procedures described in Examples 1 through 6 hereinabove and employing 7-azaindole and methyl p-tolyl sulfoxide as starting materials, the title product is obtained as a white solid, mp 215–217° C., characterized by mass spectral and HNMR analyses.

EXAMPLE 8

Preparation of 3-Iodo-1H-pyrrolo[2,3-b]pyridine

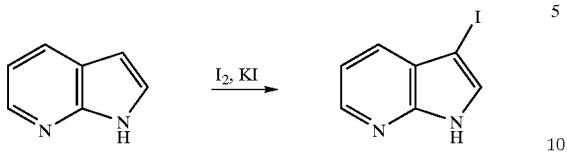

A solution of 7-azaindole (20.0 g, 169 mmol) in ethanol is treated with iodine (57.9 g, 228 mmol), potassium iodide (37.8 g, 228 mmol), and 1N aqueous NaOH (204 mL, 204 mmol). After stirring for 4 h at 20° C., the reaction is diluted with water and extracted with ethyl acetate. The organic extracts are combined and concentrated in vacuo. The resultant residue is crystallized from methanol/water to afford the title compound as a pinkish-white solid, 35.4 g, mp 201–204° C., characterized by mass spectral and HNMR analyses.

EXAMPLE 9

Preparation of 3-[(4-Fluorophenyl)thio]-1H-pyrrolo[2,3-b]pyridine

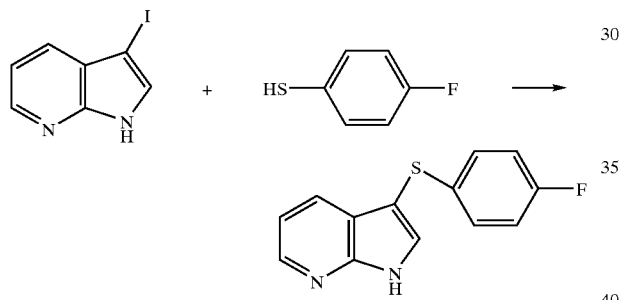

A solution of 3-iodo-1H-pyrrolo[2,3-b]pyridine (4.0 g, 16.4 mmol) in DMF is treated with 4-fluorobenzenethiol (2.09 mL, 19.7 mmol), potassium carbonate (3.40 g, 24.6 mmol), and copper iodide (4.21 g, 22.1 mmol). The reaction mixture is heated at 65° C. for 4 h, cooled, diluted with conc. aqueous $NH_4OH$ and extracted with ethyl acetate. The extracts are combined, washed with brine, dried over $MgSO_4$ and concentrated in vacuo. Chromatography (1:50 methanol:$CH_2Cl_2$) of the residue, followed by methanol/$H_2O$ crystallization affords the title compound as an off-white solid, 3.56 g, mp 183–184° C., characterized by mass spectral and NMR analyses.

EXAMPLE 10

Preparation of 3-[(4-Fluorophenyl)sulfonyl]-1H-pyrrolo[2,3-b]pyridine

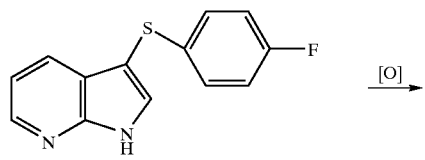

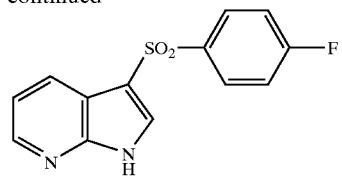

A solution of 3-[(4-fluorophenyl)thio]-1H-pyrrolo[2,3-b] pyridine (3.36 g, 13.8 mmol) in acetone is treated with a solution of $NaHCO_3$ (2.90 g, 34.5 mmol) in water. The reaction is then treated with Oxone®[1] (25.5 g, 41.4 mmol), stirred for 3 h at 20° C., diluted with water, cooled in an ice-water bath and filtered. The filtercake is washed with water and vacuum dried to afford the title compound as a white solid 1.73 g, mp 212–213° C., characterized by mass spectral and NMR analyses.

[1] $2KHSO_5 \cdot KHSO_4 \cdot K_2SO_4$, manufactured by DuPont, Wilmington, Del.

EXAMPLE 11

Preparation of 2-{3-[(4-Fluorophenyl)sulfonyl]-1H-pyrrolo[2,3-b]pyridin-1-yl}ethylamine hydrochloride

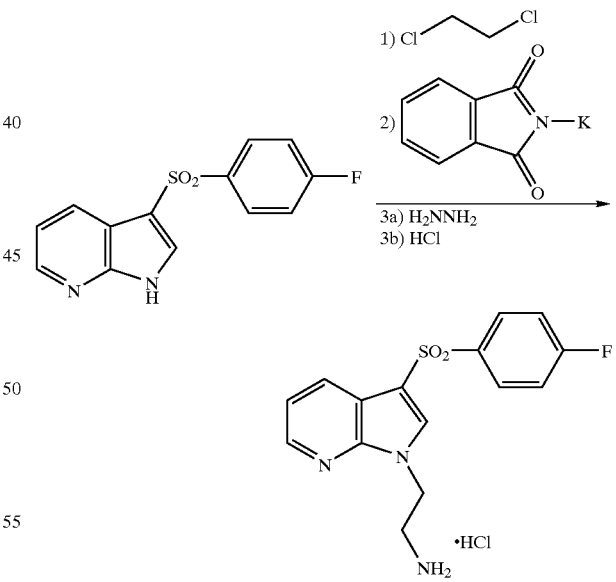

Using essentially the same procedure described in Examples 3 through 5 hereinabove and employing 3-[(4-fluorophenyl)sulfonyl]-1H-pyrrolo[2,3-b]pyridine as substrate, the title product is obtained as a white solid, mp 193–197° C., characterized by mass spectral and HNMR analyses.

EXAMPLE 12

Preparation of 2-{3-[(3-Chlorophenyl)sulfonyl]-1H-pyrrolo[2,3-b]pyridin-1-yl}ethylamine dihydrochloride

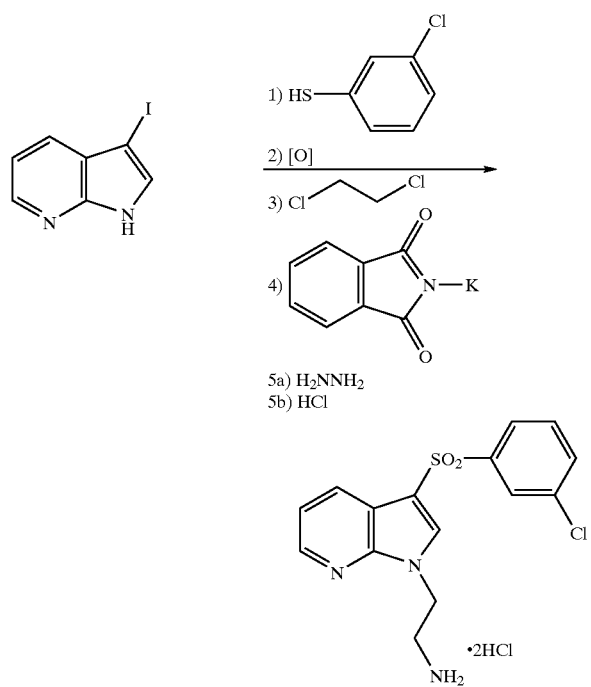

Using essentially the same procedures described hereinabove and employing 3-iodo-1H-pyrrolo[2,3-b]pyridine and 3-chlorobenzenethiol as starting materials, the title product is obtained as a white solid, mp 203–206° C., characterized by mass spectral and HNMR analyses.

EXAMPLES 13–30

Preparation of N-N-Dimethyl-N-(2-{3-[(substituted phenyl)sulfonyl]-1H-pyrrolo[2,3-b]pyridin-1-yl}ethyl)amine hydrochloride

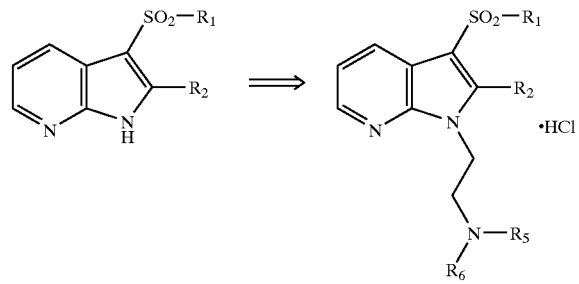

Using essentially the same procedures described in Examples 4, 5, or 6, hereinabove or using the method described by J. Alvarez-Builla, et al, Synthetic Communications, (1991) 21(4), 535–544, and employing the appropriate 3-(substituted sulfonyl)-1H-pyrrolo[2,3-b]pyridine substrate and the desired haloalkylamine, the products shown in Table I are obtained and identified by mass spectral and HNMR analyses.

TABLE I

| Ex. No. | R1 | R2 | R5 | R6 | mp ° C. |
|---|---|---|---|---|---|
| 13 | 4-F—$C_6H_4$ | H | $CH_3$ | $CH_3$ | 189–192[a] |
| 14 | 3-Cl—$C_6H_4$ | H | $CH_3$ | $CH_3$ | 182–186[a] |
| 15 | 1-naphthyl | H | $CH_3$ | $CH_3$ | 203–206 |
| 16 | 1-naphthyl | H | H | H | 148–170 |
| 17 | 3-F—$C_6H_4$ | H | H | H | 202–204 |
| 18 | $C_6H_5$ | $CH_3$ | H | H | >250[a] |
| 19 | 3-$CF_3$—$C_6H_4$ | H | $CH_3$ | $CH_3$ | 108–112 |
| 20 | 2-$CF_3$—$C_6H_4$ | H | $CH_3$ | $CH_3$ | 196–198 |
| 21 | 2-$CF_3$—$C_6H_4$ | H | H | H | 182–185[a] |
| 22 | 3-$CF_3$—$C_6H_4$ | H | H | H | 179–183 |
| 23 | 2-thienyl | H | H | H | 202–204[a] |
| 24 | 3,5-diCl—$C_6H_3$ | H | H | H | 136–140 |
| 25 | 2-thienyl | H | $CH_3$ | $CH_3$ | 212–216[a] |
| 26 | 3,5-diCl—$C_6H_3$ | H | $CH_3$ | $CH_3$ | 227–232[a] |
| 27 | 3-Cl—$C_6H_4$ | H | $CH_2$—$CH_2$—$CH_2$—$CH_2$ | | 183–185[a] |
| 28 | 3-F—$C_6H_4$ | H | $CH_2$—$CH_2$—$CH_2$—$CH_2$ | | 198–200[a] |
| 29 | 3-F—$C_6H_4$ | H | $CH_2$—$CH_2$—$CH_2$—$CH_2$—$CH_2$ | | 197–199[a] |
| 30 | 3-F—$C_6H_4$ | H | $CH_2$—$CH_2$—O—$CH_2$—$CH_2$ | | 127–129 |

[a]Dihydrochloride salt

EXAMPLE 31

Preparation of N,N-Di methyl-N-[2-(1H-pyrrolo[2,3-b]pyridin-1-yl)ethyl]amine

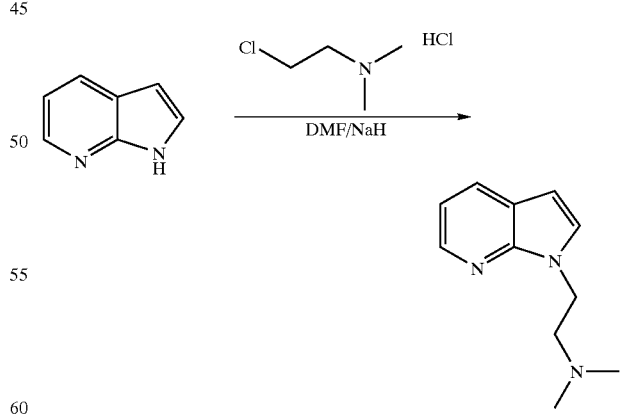

A stirred solution of 1H-pyrrolo[2,3-b]pyridine (5.00 g, 42.3 mmol) in DMF at ambient temperature is treated with 95% sodium hydride in oil (3.78 g, 150 mmol). After gas evolution subsides, the reaction mixture is treated with 2-(dimethylamino)-ethyl chloride hydrochloride (6.40 g, 44.4 mmol), stirred for 16 h and concentrated in vacuo. The resultant residue is partitioned between EtOAc and water. The organic phase is separated, dried over $MgSO_4$ and concentrated in vacuo to afford the title compound as an oil, 6.50 g (81% yield), identified by HNMR and mass spectral analyses.

EXAMPLE 32

Preparation of N,N-Dimethyl N-(2-{3-[(3-fluorophenyl)sulfonyl]-1H-pyrrolo[2,3-b]pyridin-1-yl}ethyl)amine Dihydrochloride

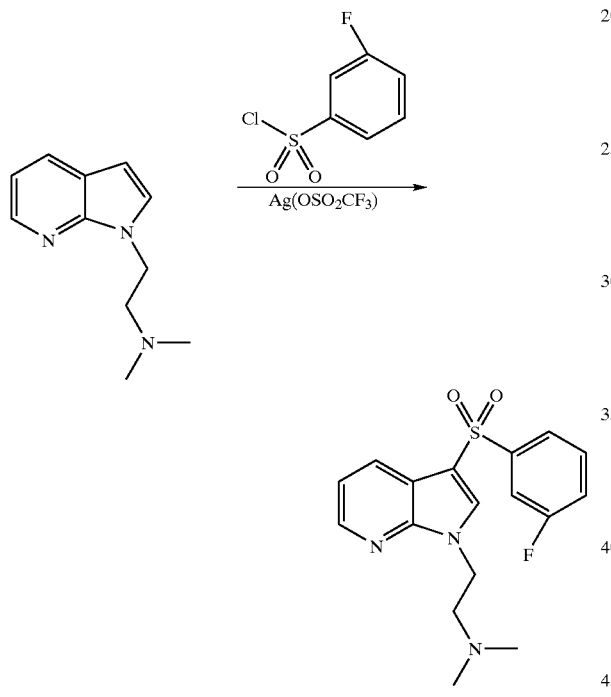

A stirred solution of N,N-dimethyl-N-[2-(1H-pyrrolo[2,3-b]pyridin-1-yl)ethyl]amine (1.66 g, 8.8 mmol) in nitrobenzene is treated with 3-fluorophenylsulfonyl chloride (1.88 g, 9.7 mmol) under nitrogen, followed by silver trifluoromethylsulfonate (2.94 g, 11.4 mmol), heated to 100° C. for 22 h, cooled and filtered through a cotton plug. The filtrate is treated with water and saturated aqueous $NaHCO_3$ and extracted with $CH_2Cl_2$. The extracts are combined, dried over $MgSO_4$ and concentrated in vacuo. The resultant residue is chromatographed eluting with 2:98 concentrated $NH_4OH$:ethanol, to afford the free amine of the title compound as a viscous oil which solidifies (1.25 g, 41%). The free amine is dissolved in warm ethanol, treated with 4M HCl in dioxane and filtered. The filtercake is dried to give the title product as a pale yellow solid, 1.07 g (29% yield), mp 191–192° C., identified by mass spectral and HNMR analyses.

EXAMPLES 33–56

Preparation of N-{[2-(3-Arylsulfonyl)-1H-pyrrolo[2,3-b]pyridin-1-yl]ethyl}amine Derivatives

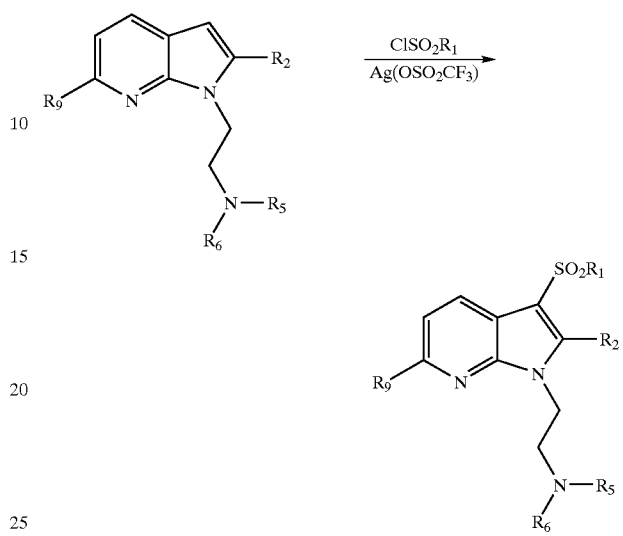

Using essentially the same procedure described hereinabove and employing the appropriately N1-substituted 1H-pyrrolo[2,3-b]pyridine substrate and the desired arylsulfonyl chloride, the compounds shown on Table II are obtained and characterized by mass spectral and HNMR analyses.

TABLE II

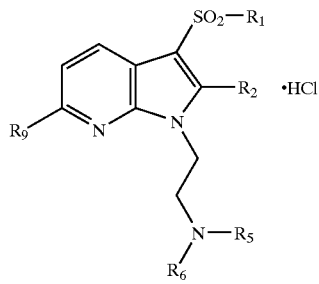

| Ex. No. | R1 | R2 | R9 | R5 | R6 | mp ° C. |
|---|---|---|---|---|---|---|
| 33 | 5-Cl-thien-2-yl | H | H | $CH_3$ | $CH_3$ | 169–171[a] |
| 34 | 6-Cl-imidazo[2,1-b][1,3]thiazol-5-yl | H | H | $CH_3$ | $CH_3$ | 180–182[a] |
| 35 | 3-Cl—$C_6H_4$ | H | H | $C_2H_5$ | $C_2H_5$ | 74–76 |
| 36 | 3-$CH_3$-5-Cl-benzothien-2-yl | H | H | $CH_3$ | $CH_3$ | 212–215 |
| 37 | 2,6-diCl—$C_6H_3$ | H | H | $CH_3$ | $CH_3$ | 220–222 |
| 38 | 2,5-diCl—$C_6H_3$ | H | H | $CH_3$ | $CH_3$ | 230–232[a] |
| 39 | 6-Cl-imidazo[2,1-b][1,3]thiazol-5-yl | H | H | benzyl | benzyl | 140–145[b] |
| 40 | 3-$CH_3$—$C_6H_4$ | H | H | $CH_3$ | $CH_3$ | 195–197 |
| 41 | $C_6H_5$ | H | Br | $CH_3$ | $CH_3$ | 182–184 |
| 42 | $C_6H_5$ | H | $OCH_3$ | $CH_3$ | $CH_3$ | 217–119 |
| 43 | $C_6H_5$ | H | Cl | $CH_3$ | $CH_3$ | 193–195 |
| 44 | 3-CN—$C_6H_4$ | H | H | $CH_3$ | $CH_3$ | 148–150 |
| 45 | 2-naphthyl | $CH_3$ | H | $CH_3$ | $CH_3$ | 238–240 |
| 46 | 3-CN—$C_6H_4$ | $CH_3$ | H | $CH_3$ | $CH_3$ | 158–160 |
| 47 | 3,5-diCl—$C_6H_3$ | $CH_3$ | H | $CH_3$ | $CH_3$ | 250–252 |
| 48 | 3-$CF_3$—$C_6H_4$ | $CH_3$ | H | $CH_3$ | $CH_3$ | 195–197 |
| 49 | 2-thienyl | $CH_3$ | H | $CH_3$ | $CH_3$ | 213–216 |

TABLE II-continued

![Structure with SO2-R1, R2, R9, R5, R6 substituents on pyrrolopyridine]·HCl

| Ex. No. | R1 | R2 | R9 | R5 | R6 | mp °C. |
|---|---|---|---|---|---|---|
| 50 | 6-Cl-imidazo[2,1-b][1,3]thiazol-5-yl | CH₃ | H | CH₃ | CH₃ | 195–199 |
| 51 | 3-F—C₆H₄ | CH₃ | H | CH₃ | CH₃ | 185–190 |
| 52 | 1-naphthyl | CH₃ | H | CH₃ | CH₃ | 135–139 |
| 53 | 2,5-diCl—C₆H₃ | CH₃ | H | CH₃ | CH₃ | 222–224 |
| 54 | 3-CH₃-5-Cl-benzothien-2-yl | CH₃ | H | CH₃ | CH₃ | 193–197 |
| 55 | 3-Cl—C₆H₄ | CH₃ | H | CH₃ | CH₃ | 210–213 |
| 56 | 5-Cl-thien-2-yl | CH₃ | H | CH₃ | CH₃ | 208–211 |

ᵃDihydrochloride salt
ᵇFoams

EXAMPLE 57

Preparation of N-(2-{3-[(3-Chlorophenyl)sulfonyl]-1H-pyrrolo[2,3-b]pyridin-1-yl}ethyl)-N-methylamine Hydrochloride

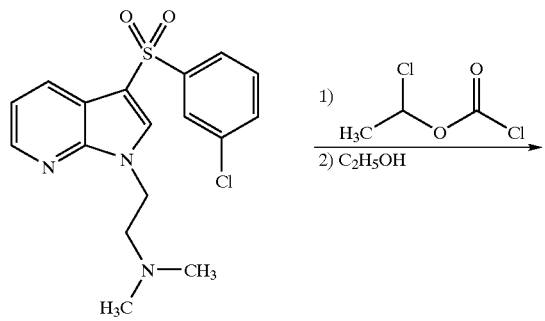

A stirred solution under nitrogen of N-(2-{3-[(3-chlorophenyl)sulfonyl]-1H-pyrrolo[2,3-b]pyridin-1-yl}ethyl)-N,N-dimethylamine (0.540 g, 1.49 mmol) in 1,2-dichloroethane is treated with 1-chloroethyl chloroformate (0.40 mL, 3.7 mmol), heated at reflux temperature for 2 h cooled, and concentrated in vacuo. The resultant residue is treated with ethanol, heated at reflux temperature for 2 h and concentrated in vacuo. This resultant residue is chromatographed using 2:98 concentrated NH₄OH:ethanol as eluent to afford the free amine of the title product as a semi-solid (311 mg, 60%). The free amine is dissolved in ethanol, treated with 4M HCl in dioxane and filtered. The filtercake is dried to give the title product as a pale yellow solid, 274 mg (48% yield), mp 263–265° C. (dec.), identified by mass spectral and HNMR analyses.

EXAMPLES 58–62

Preparation of N-{[2-(3-Arylsulfonyl)-1H-pyrrolo[2,3-b]pyridin-1-yl]ethyl}amine Derivatives

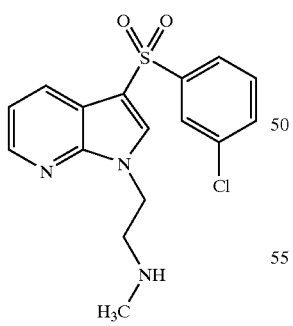

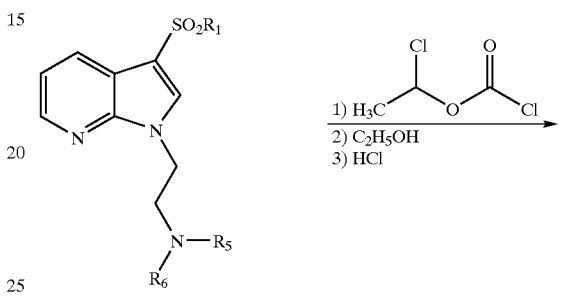

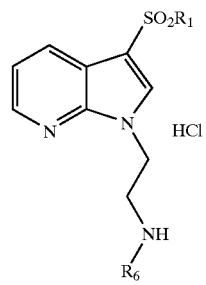

Using essentially the same procedure described hereinabove and employing the appropriate N-(N,N-disubstituted-aminoalkyl)-1H-pyrrolo[2,3-b]pyridine substrate, the compounds shown on Table III are obtained and characterized by mass spectral and HNMR analyses.

TABLE III

| Ex. No. | R1 | R6 | Mp °C. |
|---|---|---|---|
| 58 | 6-Cl-imidazo[2,1-b][1,3]thiazol-5-yl | CH₃ | 182–186 (foams) |
| 59 | 3-F—C₆H₄ | CH₃ | 255–260 |
| 60 | 3-Cl—C₆H₄ | C₂H₅ | 231–233 |
| 61 | 6-Cl-imidazo[2,1-b][1,3]thiazol-5-yl | CH₂C₆H₅ | 173–175 |
| 62 | 3-CH₃—C₆H₄ | CH₃ | 244–246 |

EXAMPLE 63

Preparation of 1-(1H-Pyrrolo[2,3-b]pyridin-1-yl)acetonitrile

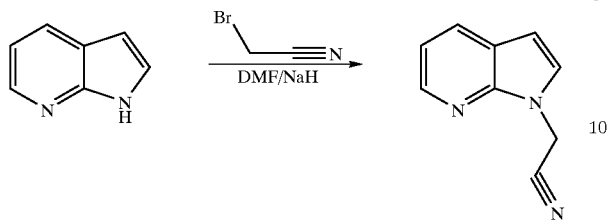

A stirred solution of 1H-pyrrolo[2,3-b]pyridine (5.06 g, 42.8 mmol) in DMF at ambient temperature is treated portionwise with 95% sodium hydride (1.10 g, 43.5 mmol). After gas evolution subsides, the reaction mixture is treated with bromoacetonitrile (3.00 mL, 43.1 mmol), stirred for 16 h, and concentrated in vacuo. The resultant residue is partitioned between EtOAc and water. The organic phase is separated, dried over MgSO₄ and concentrated in vacuo. This residue is chromatographed eluting with 1:3 EtOAc:hexanes to afford the title compound as a waxy solid, mp 77–79° C., identified by HNMR and mass spectral analyses.

EXAMPLE 64

Preparation of 1-[3-(Phenylsulfonyl)-1H-pyrrolo[2,3-b]pyridin-1-yl)acetonitrile

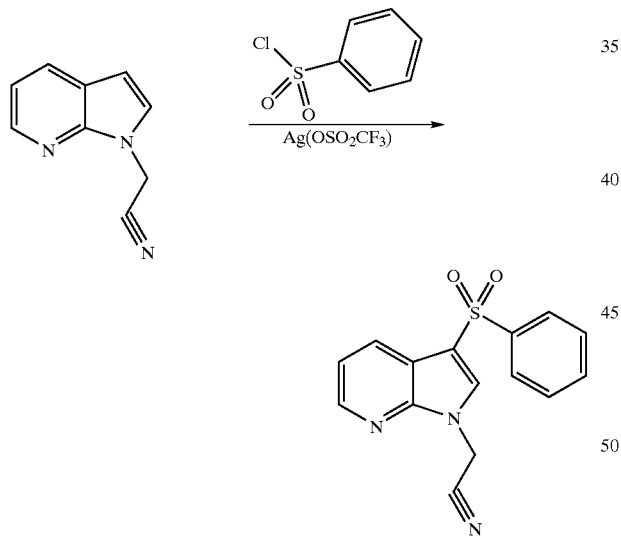

A stirred solution of 1-(1H-pyrrolo[2,3-b]pyridin-1-yl)acetonitrile (0.68 g, 4.33 mmol) in nitrobenzene is treated with benzenesulfonyl chloride (0.57 mL, 4.4 mmol) and silver trifluoromethanesulfonate (1.50 g, 5.8 mmol), heated at 125° C. for 16 h, cooled and partitioned between saturated aqueous NaHCO₃ and CH₂Cl₂. The organic phase is dried over MgSO₄ and concentrated in vacuo. The resultant residue is chromatographed eluting initially with 1:4 EtOAc:hexanes and then with 1:2 EtOAc:hexanes to afford the title compound as a tan solid, 0.70 g (54% yield), mp 140–142° C., identified by mass spectral and HNMR analyses.

EXAMPLE 65

Preparation of 2-[3-(phenylsulfonyl)-1H-pyrrolo[2,3-b]pyridin-1-yl]ethylamine

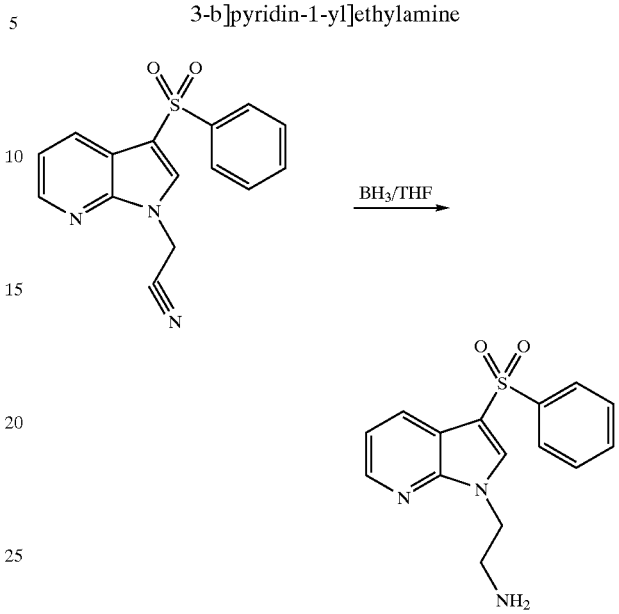

A portion of 3-(phenylsulfonyl)-1H-pyrrolo[2,3-b]pyridin-1-yl]acetonitrile (0.30 g, 1.00 mmol) is treated with 1.0 M borane in tetrahydrofuran (THF) (4.0 mL, 4.0 mmol) in 0.5 mL portions at ambient temperature, stirred for 16 h, treated with 2.0 M HCl (15 mL), heated at 100° C. for 2 h, cooled in an ice bath, treated with 2.5 M aqueous NaOH, and extracted with ether. The extracts are combined, dried over MgSO₄ and concentrated in vacuo to afford the title compound as an oil, 0.180 g (60% yield), identified by HNMR and mass spectral analyses.

EXAMPLES 66–68

Preparation of [3-(Arylsulfonyl)-1H-Pyrrolo[2,3-b]pyridin-1-yl]alkylamine Derivatives

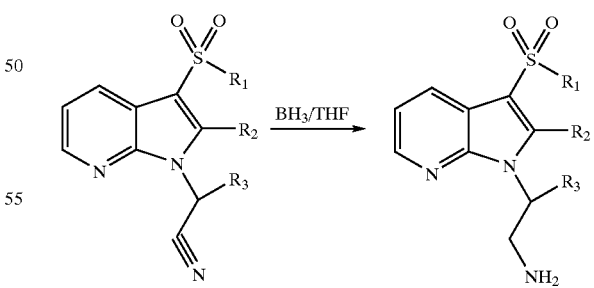

Using essentially the same procedures described in Examples 64 and 65 hereinabove and employing the appropriate 3-arylsulfonyl-1H-pyrrolo[2,3-b]pyridine-1-acetonitrile substrate, the compounds shown on Table IV are obtained and characterized by mass spectral and HNMR analyses.

TABLE IV

| Ex. No. | R1 | R2 | R3 | Mp °C. |
|---|---|---|---|---|
| 66 | 3-F—C$_6$H$_4$ | CH$_3$ | H | 239–241[a] |
| 67 | 2-naphthyl | H | H | 233–238[a] |
| 68 | C$_6$H$_5$ | H | CH$_3$ | 180–185[a] |

[a]Hydrochloride

EXAMPLE 69

Preparation of 4-Nitro-3-[(phenylsulfonyl)methyl]-pyridine-N-oxide

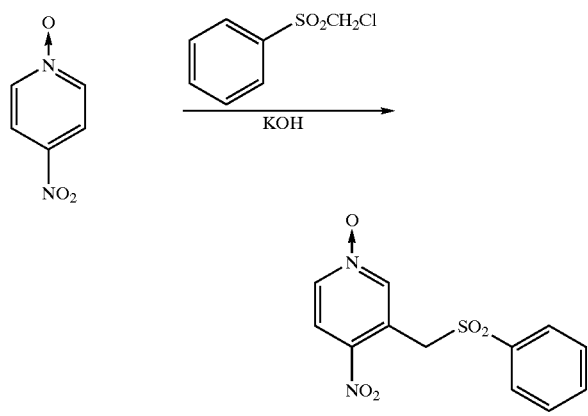

Adapting the procedure of Makosza, et al, Liebigs Ann. Chem., 1984, 8–14, a stirred mixture of 4-nitro-pyridine-N-oxide (1.40 g, 10.0 mmol) and chloromethylphenylsulfone (1.92 g, 10.0 mmol) in DMSO (25 mL) in a cold water bath is treated with a solution of KOH (4.0 g, 71 mmol) in DMSO, stirred for 45 min, poured into 1.0 M hydrochloric acid and water and extracted with CH$_2$Cl$_2$. The aqueous phase is filtered and the filtercake is dried in vacuo to afford the title compound, 1.20 g (41% yield). The organic extracts are combined, dried over MgSO$_4$ and concentrated in vacuo. The resultant wet solid is heated in boiling ethanol:water (4:1) and filtered. The filtrate is cooled, concentrated and filtered. This filtercake is dried in vacuo to afford an additional portion of the title compound, 0.967 g (74% total yield), mp 219–220° C., identified by mass spectral and HNMR analyses.

EXAMPLE 70

Preparation of 3-Phenylsulfonyl-1H-pyrrolo[3,2-c]pyridine

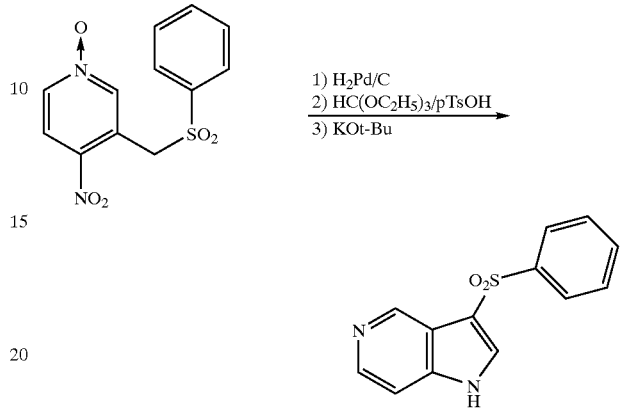

A mixture of 4-nitro-3-[(phenylsulfonyl)methyl]-pyridine-N-oxide (1.43 g, 4.90 mmol) in methanol is heated with ammonium formate (1.54 g, 24.5 mmol) and 10% palladium on carbon (0.50 g) at 50° C. for 24 h, treated with additional ammonium formate (0.63 g, 10 mmol), heated at reflux for 30 h, cooled and filtered. The filtrate is concentrated in vacuo. The resultant residue is suspended in ethanol:water and filtered to remove residual catalyst. This filtrate is concentrated, cooled and filtered. The filtercake is dried to afford a tan solid (0.60 g). This solid (0.55 g) is admixed with triethylorthoformate (1.84 mL, 11.1 mmol), para-toluenesulfonic acid (pTsOH) monohydrate (42 mg, 0.22 mmol) and 1,2-dichloroethane, heated at reflux for 7 h and concentrated in vacuo. The resultant residue is dispersed in tetrahydrofuran, treated with 1.0 M KO-t-Bu in tetrahydrofuran (3.1 mL, 3.1 mmol), stirred for 2 h, treated with saturated aqueous NH$_4$Cl and water and extracted with CH$_2$Cl$_2$. The extracts are combined, dried over MgSO$_4$ and concentrated in vacuo. The resultant orange solid residue is chromatographed eluting initially with EtOAc, then with 10:90 ethanol:EtOAc to afford the title compound as an off-white solid, 330 mg (58% yield), mp 261–263° C., identified by mass spectral and HNMR analyses.

EXAMPLE 71

Preparation of N,N-Dimethyl-N-{2-[3-(phenylsulfonyl)-1H-pyrrolo[3,2-c]pyridin-1-yl]ethyl}amine Dihydrochloride

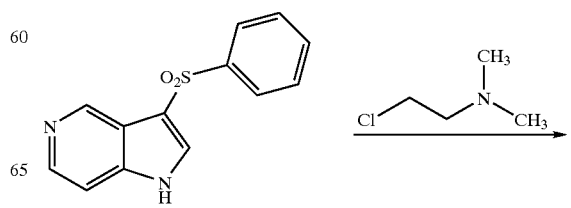

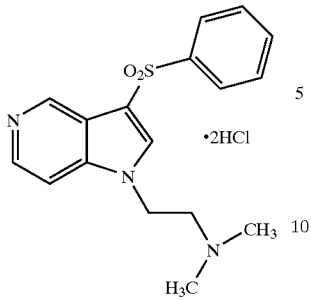

Using essentially the same procedure described in Example 6 hereinabove and employing 3-phenylsulfonyl-1H-pyrrolo[3,2-c]pyridine, ambient reaction temperatures and a 24 h reaction time period, the title compound is obtained as an off-white solid, mp 255–257° C., identified by mass spectral and HNMR analyses.

EXAMPLE 72

Preparation of 6-Methoxy-3-nitro-2-[(phenylsulfonyl)methyl]-pyridine

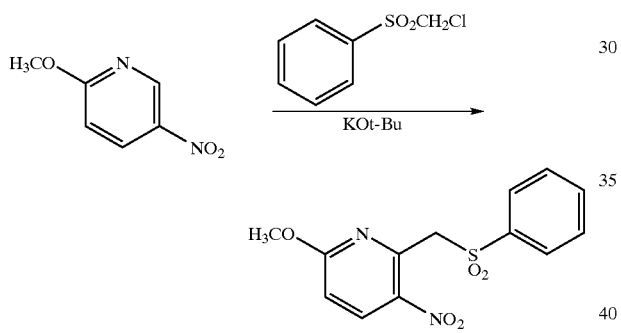

A 1M KOt-Bu solution in tetrahydrofuran (50 mL, 50 mmol) is cooled to −40° C., treated portion-wise with a solution of chloromethyl phenyl sulfone (4.39 g, 23.0 mmol) and then with a solution of 2-methoxy-5-nitropyridine (3.55 g, 23.0 mmol) in tetrahydrofuran, stirred for 45 min at −40° C., treated with glacial acetic acid (3.0 g, 50 mmol) and filtered. The filtercake is air-dried to give the title compound as a tan solid, 5.70 g (80% yield), mp 147–149° C., identified by mass spectral and HNMR analyses.

EXAMPLE 73

Preparation of 3-Amino-6-methoxy-2-[(phenylsulfonyl)methyl]-pyridine

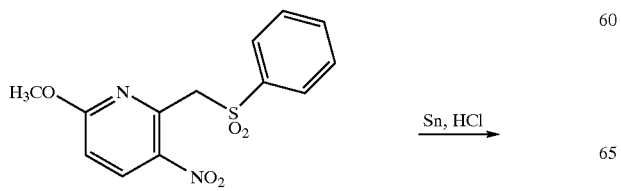

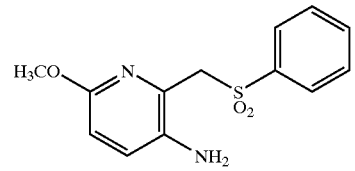

A stirred mixture of 6-methoxy-3-nitro-2-[(phenylsulfonyl)methyl]-pyridine (6.17 g, 20.0 mmol) in methanol and concentrated HCl (50 mL) is treated with thin strips of tin foil (10.0 g, 84.2 mmol), heated at 60° C. for 20 h, and filtered hot. The filtrate is poured over ice and 2.5N aqueous NaOH, stirred for 0.5 h and filtered. The filtercake is air-dried to afford the title compound as a white solid 5.26 g (94% yield), identified by mass spectral and HNMR analyses.

EXAMPLE 74

Preparation of N-{6-Methoxy-[2-(phenylsulfonyl)methyl]pyridin-3-yl}-formimidic Acid Ethyl Ester

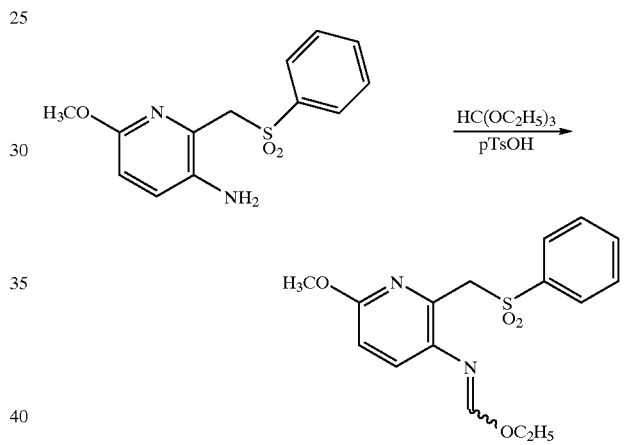

A stirred mixture of 3-amino-6-methoxy-2-[(phenylsulfonyl)methyl]-pyridine (2.40 g, 8.62 mmol) in triethyl orthoformate (20 mL) and p-toluenesulfonic acid (pTsOH) monohydrate (0.15 g, 0.788 mmol) is heated at 155° C. for 48 h and concentrated in vacuo. The resultant residue is diluted with hexanes and filtered to give the title product as a tan solid, 2.54 g (88% yield), identified by mass spectral and HNMR analyses.

EXAMPLE 75

Preparation of 5-Methoxy-3-phenylsulfonyl-1H-pyrrolo[3,2-b]pyridine

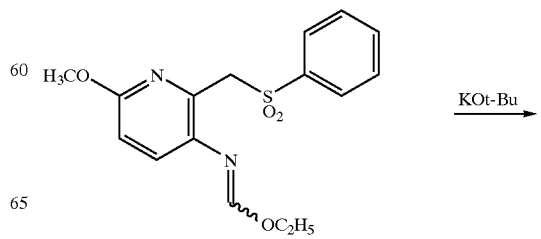

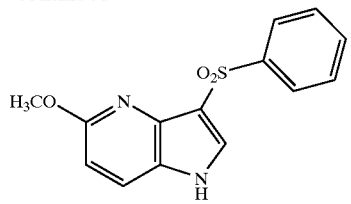

A stirred solution of N-{6-methoxy-[2-(phenylsulfonyl)methyl]-pyridin-3-yl}-formimidic acid ethyl ester (2.54 g, 7.60 mmol) in DMSO is treated with powdered KOt-Bu (4.50 9, 38.0 mmol), stirred at ambient temperature for 4 h, treated with 10% aqueous $NH_4Cl$ and extracted with EtOAc. The extracts are combined, dried over $MgSO_4$ and concentrated in vacuo. The resultant residue is recrystallized from EtOAc to afford the title compound as a tan solid, 0.42 g (19% yield), mp 223–225° C., identified by mass spectral and HNMR analyses.

EXAMPLE 76

Preparation of N,N-Dimethyl-N-{2-[3-(phenylsulfonyl)-1H-pyrrolo[3,2-b]pyridin-1-yl]ethyl}amine Dihydrochloride

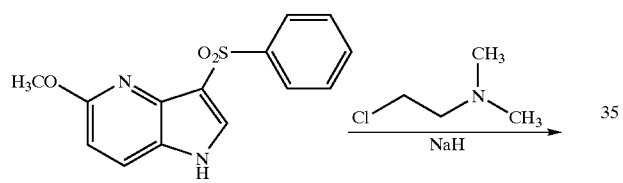

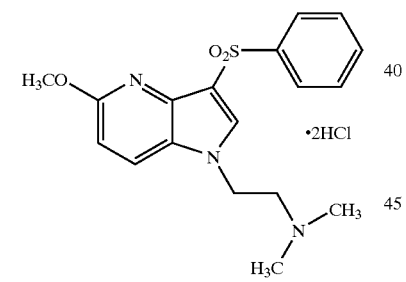

A stirred solution of 5-methoxy-3-phenylsulfonyl-1H-pyrrolo[3,2-b]pyridine (0.288 g, 1.00 mmol) in dry dimethyl formamide is treated with 95% NaH (0.075 g, 2.97 mmol), stirred at ambient temperature until gas evolution subsides, treated with 2-(dimethylamino)ethylchloride hydrochloride (0.200 g, 1.39 mmol), stirred for 16 h at 80° C., concentrated in vacuo and partitioned between water and EtOAc. The organic phase is dried over $MgSO_4$ and concentrated in vacuo. The resultant residue is chromatographed eluting with EtOAc, then 1:9 $CH_3OH$:EtOAc, to obtain a semi-solid (0.216 g, 60% yield of the free amine). The semi-solid is dissolved in ethanol and treated with 4N HCl in dioxane and filtered. The filtercake is dried and triturated with ether to afford the title compound as a white solid, 0.19 g, mp 212–214° C., identified by mass spectral and HNMR analyses.

EXAMPLE 77

Preparation of N,N-Dimethyl-N-(2-{3-[(3-fluorophenyl)sulfonyl]-1H-pyrrolo[3,2-b]pyridin-1-yl}ethyl)amine Dihydrochloride

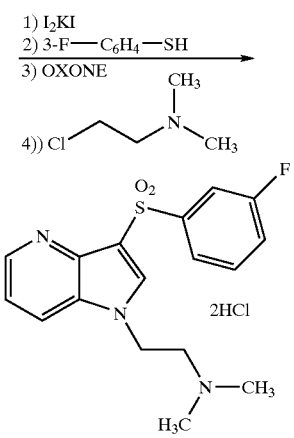

Using essentially the same procedures described in Examples 6, 8, 9 and 10 hereinabove and employing 1-H-pyrrolo[3,2-b]pyridine as the starting material, the title compound is obtained as a white solid, mp 163–165° C., identified by mass spectral and HNMR analyses.

EXAMPLES 78–81

Preparation of N-{2-[3-(Arylsulfonyl)-1H-pyrrolo[3,2-b]pyridin-1-yl]ethyl}amine Derivatives

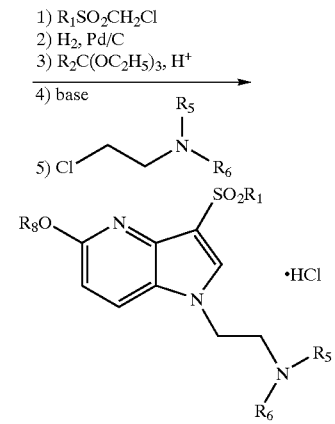

Using essentially the same procedures described in Examples 72–76 hereinabove and employing the appropriately substituted nitropyridine starting material and arylsulfonyl chloride and chloroethylamine reagents, the compounds shown on Table V are obtained and identified by mass spectral and HNMR analyses

TABLE V

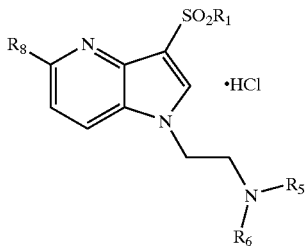

| Ex. No. | R1 | R8 | R5 | R6 | mp ° C. |
|---|---|---|---|---|---|
| 78 | 4-Br—C$_6$H$_4$ | OCH$_3$ | CH$_3$ | CH$_3$ | 225–226 |
| 79 | 3-F—C$_6$H$_4$ | OCH$_3$ | CH$_3$ | CH$_3$ | 208–212 |
| 80 | 1-naphthyl | OCH$_3$ | CH$_3$ | CH$_3$ | 233–235 |
| 81 | C$_6$H$_5$ | Cl | CH$_3$ | CH$_3$ | 244–246 |

EXAMPLE 82

Comparative Evaluation of 5-HT6 Binding Affinity of Test Compounds

The affinity of test compounds for the serotonin 5-HT6 receptor is evaluated in the following manner. Cultured Hela cells expressing human cloned 5-HT6 receptors are harvested and centrifuged at low speed (1,000×g) for 10.0 min to remove the culture media. The harvested cells are suspended in half volume of fresh physiological phosphate buffered saline solution and recentrifuged at the same speed. This operation is repeated. The collected cells are then homogenized in ten volumes of 50 mM Tris.HCl (pH 7.4) and 0.5 mM EDTA. The homogenate is centrifuged at 40,000×g for 30.0 min and the precipitate is collected. The obtained pellet is resuspended in 10 volumes of Tris.HCl buffer and recentrifuged at the same speed. The final pellet is suspended in a small volume of Tris.HCl buffer and the tissue protein content is determined in aliquots of 10–25 µl volumes. Bovine Serum Albumin is used as the standard in the protein determination according to the method described in Lowry et al., *J. Biol. Chem.*, 193:265 (1951). The volume of the suspended cell membranes is adjusted to give a tissue protein concentration of 1.0 mg/ml of suspension. The prepared membrane suspension (10 times concentrated) is aliquoted in 1.0 ml volumes and stored at −70° C. until used in subsequent binding experiments.

Binding experiments are performed in a 96 well microtiter plate format, in a total volume of 200 µl. To each well is added the following mixture: 80.0 µl of incubation buffer made in 50 mM Tris.HCl buffer (pH 7.4) containing 10.0 mM MgCl$_2$ and 0.5 mM EDTA and 20 µl of [$^3$H]-LSD (S.A., 86.0 Ci/mmol, available from Amersham Life Science), 3.0 nM. The dissociation constant, $K_D$ of the [$^3$H]LSD at the human serotonin 5-HT6 receptor is 2.9 nM, as determined by saturation binding with increasing concentrations of [$^3$H]LSD. The reaction is initiated by the final addition of 100.0 µl of tissue suspension. Nonspecific binding is measured in the presence of 10.0 µM methiothepin. The test compounds are added in 20.0 µl volume.

The reaction is allowed to proceed in the dark for 120 min at room temperature, at which time, the bound ligand-receptor complex is filtered off on a 96 well unifilter with a Packard Filtermate® 196 Harvester. The bound complex caught on the filter disk is allowed to air dry and the radioactivity is measured in a Packard TopCount® equipped with six photomultiplier detectors, after the addition of 40.0 µl Microscint®-20 scintillant to each shallow well. The unifilter plate is heat-sealed and counted in a PackardTopCount® with a tritium efficiency of 31.0%.

Specific binding to the 5-HT6 receptor is defined as the total radioactivity bound less the amount bound in the presence of 10.0 µM unlabeled methiothepin. Binding in the presence of varying concentrations of test compound is expressed as a percentage of specific binding in the absence of test compound. The results are plotted as log % bound versus log concentration of test compound. Nonlinear regression analysis of data points with a computer assisted program Prism® yielded both the IC$_{50}$ and the K$_i$ values of test compounds with 95% confidence limits. A linear regression line of data points is plotted, from which the IC$_{50}$ value is determined and the K$_i$ value is determined based upon the following equation:

$$K_i = IC_{50}/(1+L/K_D)$$

where L is the concentration of the radioactive ligand used and K$_D$ is the dissociation constant of the ligand for the receptor, both expressed in nM.

Using the following Ki values are determined and compared to those values obtained by representative compounds known to demonstrate binding to the 5-HT6 receptor. The data are shown in Table VI, below.

TABLE VI

| Test Compound (Ex. No.) | 5-HT6 Binding Ki (nM) |
|---|---|
| 5 | 6 |
| 6 | 23 |
| 7 | 9 |
| 11 | 22 |
| 12 | 20 |
| 13 | 50 |
| 14 | 2 |
| 15 | 1 |
| 16 | 2 |
| 17 | 6 |
| 18 | 5 |
| 19 | 5 |
| 20 | 11 |
| 21 | 2 |
| 22 | 2 |
| 23 | 9 |
| 24 | 3 |
| 25 | 15 |
| 26 | 4 |
| 27 | 45 |
| 28 | 88 |
| 29 | 158 |
| 30 | 403 |
| 32 | 5 |
| 33 | 4 |
| 34 | 2 |
| 35 | 20 |
| 36 | 102 |
| 37 | 9 |
| 38 | 12 |
| 39 | 212 |
| 40 | 10 |
| 41 | 41 |
| 42 | 39 |
| 43 | 27 |
| 44 | 63 |
| 45 | 10 |
| 46 | 10 |
| 47 | 7 |
| 48 | 2 |

TABLE VI-continued

| Test Compound | 5-HT6 Binding Ki (nM) |
|---|---|
| 49 | 14 |
| 50 | 1 |
| 51 | 3 |
| 52 | 3 |
| 53 | 11 |
| 54 | 94 |
| 55 | 4 |
| 56 | 2 |
| 57 | 0.3 |
| 58 | 1 |
| 59 | 1 |
| 60 | 3 |
| 61 | 9 |
| 62 | 1 |
| 66 | 2 |
| 67 | 24 |
| 68 | 14 |
| 76 | 56 |
| 77 | 200 |
| 78 | 4 |
| 79 | 11 |
| 80 | 2 |
| 81 | 214 |
| Comparative Examples | |
| Clozapine | 6.0 |
| Loxapine | 41.4 |
| Bromocriptine | 23.0 |
| Methiothepin | 8.3 |
| Mianserin | 44.2 |
| Olanzepine | 19.5 |

As can be seen from the results set forth above, the compounds of the present invention demonstrate significant affinity for the 5-HT6 receptor.

What is claimed is:

1. A compound of formula I

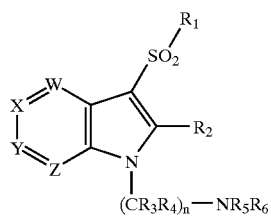

(I)

wherein

W is N or $CR_7$;

X is N or $CR_8$;

Y is N or $CR_9$;

Z is N or $CR_{10}$ with the proviso that only one of W, X, Y and Z must be N;

n is an integer of 2, 3, 4 or 5;

$R_1$ is an optionally substituted $C_1$–$C_6$alkyl, $C_3$–$C_7$cycloalkyl, aryl, or 5- to 10-membered heteroaryl ring system containing 1, 2 or 3 heteroatoms selected from N, O or S group or an optionally substituted 8- to 13-membered bicyclic or tricyclic ring system having a N atom at the bridgehead and optionally containing 1, 2 or 3 additional heteroatoms selected from N, O or S;

$R_2$ is H, halogen, or a $C_1$–$C_6$alkyl, $C_1$–$C_6$alkoxy, $C_3$–$C_7$cycloalkyl, aryl or 5- to 10-membered heteroaryl ring system containing 1, 2 or 3 heteroatoms selected from N, O or S group each optionally substituted;

$R_3$ and $R_4$ are each independently H or an optionally substituted $C_1$–$C_8$alkyl group;

$R_5$ and $R_6$ are each independently H or a $C_1$–$C_6$alkyl, $C_2$–$C_6$alkenyl, $C_3$–$C_7$cycloalkyl, 5- to 7-membered cycloheteroalkyl ring system containing 1 or 2 heteroatoms selected from N, O or S optionally containing one double bond, aryl or 5- to 10-membered heteroaryl ring system containing 1, 2 or 3 heteroatoms selected from N, O or S group each optionally substituted or $R_5$ and $R_6$ may be taken together with the atom to which they are attached to form an optionally substituted 5- to 8-membered ring optionally containing an additional heteroatom selected from O, $NR_{11}$ or $SO_m$; $R_7$, $R_8$, $R_9$ and $R_{10}$ are independently H, halogen, CN, $OCO_2R_{12}$, $CO_2R_{13}$, $CONR_{14}R_{15}$, $SO_pR_{16}$, $NR_{17}R_{18}$, $OR_{19}$, $COR_{20}$, or a $C_1$–$C_6$alkyl, $C_2$–$C_6$alkenyl, $C_2$–$C_6$alkynyl, $C_3$–$C_7$cycloalkyl, 5- to 7-membered cycloheteroalkyl ring system containing 1 or 2 heteroatoms selected from N, O or S optionally containing one double bond, aryl or 5- to 10-membered heteroaryl ring system containing 1, 2 or 3 heteroatoms selected from N, O or S group each optionally substituted;

$R_{11}$, $R_{12}$, $R_{13}$, $R_{16}$, $R_{19}$ and $R_{20}$ are each independently H or a $C_1$–$C_6$alkyl, $C_2$–$C_6$alkenyl, $C_2$–$C_6$alkynyl, $C_3$–$C_6$cycloalkyl, 5- to 7-membered cycloheteroalkyl ring system containing 1 or 2 heteroatoms selected from N, O or S optionally containing one double bond, aryl or 5- to 10-membered heteroaryl ring system containing 1, 2 or 3 heteroatoms selected from N, O or S group each optionally substituted;

$R_{14}$ and $R_{15}$ are each independently H or an optionally substituted $C_1$–$C_6$alkyl group or $R_{14}$ and $R_{15}$ may be taken together with the atom to which they are attached to form a 5- to 7-membered ring optionally containing another heteroatom selected from O, $NR_{22}$ or S;

$R_{17}$ and $R_{18}$ are each independently H or an optionally substituted $C_1$–$C_4$alkyl group or $R_{17}$ and $R_{18}$ may be taken together with the atom to which they are attached to form a 5- to 7-membered ring optionally containing another heteroatom selected from O, $NR_{21}$ or $SO_x$; $R_{21}$ and $R_{22}$ are each independently H or a $C_1$–$C_6$alkyl, $C_2$–$C_6$alkenyl, $C_3$–$C_7$cycloalkyl 5- to 7-membered cycloheteroalkyl ring system containing 1 or 2 heteroatoms selected from N, O or S optionally containing one double bond, aryl or 5- to 10-membered heteroaryl ring system containing 1, 2 or 3 heteroatoms selected from N, O or S group each optionally substituted; and m, p and x are each independently 0 or an integer of 1 or 2; or a pharmaceutically acceptable salt thereof.

2. The compound according to claim 1 wherein W or Z is N.

3. The compound according to claim 1 wherein n is 2.

4. The compound according to claim 1 wherein $R_1$ is an optionally substituted phenyl, naphthyl or imidazothiazolyl group.

5. The compound according to claim 2 wherein W is $CR_7$; X is $CR_8$; and Y is $CR_9$.

6. The compound according to claim 3 wherein $R_3$ and $R_4$ are H.

7. The compound according to claim 5 wherein n is 2 and $R_2$ is H.

8. The compound according to claim 7 wherein $R_1$ is phenyl optionally substituted with halogen, 1-naphthyl or 6-Cl-imidazo[1,2-b][1,3]thiazol-5-yl; $R_3$, $R_4$, $R_7$, $R_8$ and $R_9$ are H; and $R_5$ and $R_6$ are each independently H or $C_1$–$C_3$alkyl.

9. The compound according to claim 1 selected from the group consisting of:

2-[3-(phenylsulfonyl)-1H-pyrrolo[2,3-b]pyridin-1-yl]ethylamine;
2-[3-(phenylsulfonyl)-1H-pyrrolo[2,3-c]pyridin-1-yl]ethylamine;
2-[3-(phenylsulfonyl)-1H-pyrrolo[3,2-c]pyridin-1-yl]ethylamine;
2-{3-[(4-fluorophenyl)sulfonyl]-1H-pyrrolo[3,2-b]pyridin-1-yl}ethylamine;
2-{3-[(4-methylphenyl)sulfonyl]-1H-pyrrolo[2,3-b]pyridin-1-yl}ethylamine;
2-[3-(naphth-1-yl)sulfonyl)-1H-pyrrolo[2,3-b]pyridin-1-yl]ethylamine;
2-{3-[(6-chloro-imidazo[2,1-b][1,3]thiazol-5-yl)sulfonyl]-1H-pyrrolo[2,3-b]pyridin-1-yl}ethylamine;
2-{3-[(3-chlorophenyl)sulfonyl]-1H-pyrrolo[2,3-b]pyridin-1-yl}ethylamine;
2-{3-[(2-chlorophenyl)sulfonyl]-1H-pyrrolo[2,3-c]pyridin-1-yl}ethylamine;
2-{3-[(3-methoxyphenyl)sulfonyl]-1H-pyrrolo[3,2-c]pyridin-1-yl}ethylamine;
2-{3-[(4-fluorophenyl)sulfonyl]-1H-pyrrolo[3,2-b]pyridin-1-yl}ethylamine;
N,N-dimethyl-N-(2-{3-[(3-fluorophenyl)sulfonyl]-1H-pyrrolo[2,3-b]pyridin-1-yl}ethyl)amine;
N,N-dimethyl-N-{2-[3-(naphth-1-ylsulfonyl)-1H-pyrrolo[2,3-b]pyridin-1-yl]ethyl}amine;
N,N-dimethyl-N-(2-{3-[(6-chloroimidazo[1,2-b][1,3]thiazol-5-yl)sulfonyl]-1H-pyrrolo[2,3-b]pyridin-1-yl}ethyl)amine;
N,N-dimethyl-N-(2-{3-[(3-chlorophenyl)sulfonyl]-1H-pyrrolo[2,3-b]pyridine-1-yl}ethyl)amine;
3-[3-(phenylsulfonyl)-1H-pyrrolo[2,3-b]pyridin-1-yl]propan-1-amine;
3-[3-(phenylsulfonyl)-1H-pyrrolo[2,3-c]pyridin-1-yl]propan-1-amine;
3-[3-(phenylsulfonyl)-1H-pyrrolo[3,2-c]pyridin-1-yl]propan-1-amine;
3-{3-[(4-fluorophenyl)sulfonyl]-1H-pyrrolo[3,2-b]pyridin-1-yl}propan-1-amine;
2-{6-chloro-3-[(3-chlorophenyl)sulfonyl]-1H-pyrrolo[2,3-b]pyridin-1-yl}ethylamine;
2-{7-chloro-3-[(2-chlorophenyl)sulfonyl]-1H-pyrrolo[2,3-c]pyridin-1-yl}ethylamine;
4-{3-[(3-methoxyphenyl)sulfonyl]-1H-pyrrolo[3,2-c]pyridin-1-yl}butan-1-amine;
4-{3-[(4-fluorophenyl)sulfonyl]-1H-pyrrolo[3,2-b]pyridin-1-yl}butan-1-amine;
N,N-dimethyl-N-{2-[3-(phenylsulfonyl)-1H-pyrrolo[2,3-c]pyridin-1-yl]ethyl}amine;
N,N-dimethyl-N-{2-[3-(phenylsulfonyl)-1H-pyrrolo[3,2-c]pyridin-1-yl]ethyl}amine;
N,N-dimethyl-N-{2-[3-(thien-2-yl)-1H-pyrrolo[2,3-b]pyridin-1-yl]ethyl}amine;
N,N-dimethyl-N-{2-[3-(naphth-1-yl)-1H-pyrrolo[2,3-b]pyridin-1-yl]ethyl}amine;
N,N-dimethyl-N-(2-{3-[(4-fluorophenyl)sulfonyl]-1H-pyrrolo[3,2-b]pyridin-1-yl}ethyl)amine;
N-methyl-N-(2-{3-[(3-chlorophenyl)sulfonyl]-1H-pyrrolo[2,3-b]pyridin-1-yl}ethyl)amine;
N-methyl-N-(2-{3-[(3-fluorophenyl)sulfonyl]-1H-pyrrolo[2,3-b]pyridin-1-yl}ethyl)amine;
N-methyl-N-{2-[3-(naphth-1-ylsulfonyl)-1H-pyrrolo[2,3-b]pyridin-1-yl]ethyl}amine;
N-methyl-N-(2-{3-[(6-chloroimidazo[1,2-b][1,3]thiazol-5-yl)sulfonyl]-1H-pyrrolo[2,3-b]pyridin-1-yl}ethyl)amine;
N-methyl-N-(2-{3-[(2-chlorophenyl)sulfonyl]-1H-pyrrolo[2,3-c]pyridin-1-yl}ethyl)amine;
N-methyl-N-(2-{3-[(3-methoxyphenyl)sulfonyl]-1H-pyrrolo[3,2-c]pyridin-1-yl}ethyl)amine;
N-benzyl-N-(2-{3-[(4-fluorophenyl)sulfonyl]-1H-pyrrolo[3,2-b]pyridin-1-yl}ethyl)amine;
N,N-dibenzyl-3-[3-(phenylsulfonyl)-1H-pyrrolo[2,3-b]pyridin-1-yl]propan-1-amine;
3-[3-(phenylsulfonyl)-1H-pyrrolo[2,3-c]pyridin-1-yl]propan-1-amine;
3-[3-(phenylsulfonyl)-1H-pyrrolo[3,2-c]pyridin-1-yl]propan-1-amine; and the pharmaceutically acceptable salts thereof.

10. A pharmaceutical composition which comprises a pharmaceutically acceptable carrier and an effective amount of a compound of formula I

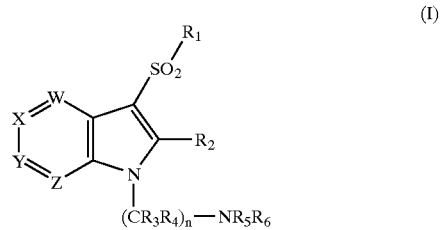

wherein
W is N or $CR_7$;
X is N or $CR_8$;
Y is N or $CR_9$;
Z is N or $CR_{10}$ with the proviso that only one of W, X, Y and Z must be N;
n is an integer of 2, 3, 4 or 5;
$R_1$ is an optionally substituted $C_1$–$C_6$alkyl, $C_3$–$C_7$cycloalkyl, aryl, or 5- to 10-membered heteroaryl ring system containing 1, 2 or 3 heteroatoms selected from N, O or S group or an optionally substituted 8- to 13-membered bicyclic or tricyclic ring system having a N atom at the bridgehead and optionally containing 1, 2 or 3 additional heteroatoms selected from N, O or S;
$R_2$ is H, halogen, or a $C_1$–$C_6$alkyl, $C_1$–$C_6$alkoxy, $C_3$–$C_7$cycloalkyl, aryl or 5- to 10-membered heteroaryl ring system containing 1, 2 or 3 heteroatoms selected from N, O or S group each optionally substituted;
$R_3$ and $R_4$ are each independently H or an optionally substituted $C_1$–$C_6$alkyl group;
$R_5$ and $R_6$ are each independently H or a $C_1$–$C_6$alkyl, $C_2$–$C_6$alkenyl, $C_2$–$C_6$alkynyl, $C_3$–$C_7$cycloalkyl, 5- to 7-membered cycloheteroalkyl ring system containing 1 or 2 heteroatoms selected from N, O or S optionally containing one double bond, aryl or 5- to 10-membered heteroaryl ring system containing 1, 2 or 3 heteroatoms selected from N, O or S group each optionally substituted or $R_5$ and $R_6$ may be taken together with the atom to which they are attached to form an optionally substituted 5- to 8-membered ring optionally containing an additional heteroatom selected from O, $NR_{11}$ or $SO_m$;

R$_7$, R$_8$, R$_9$ and R$_{10}$ are independently H, halogen, CN, OCO$_2$R$_{12}$, CO$_2$R$_{13}$, CONR$_{14}$R$_{15}$, SO$_p$R$_{16}$, NR$_{17}$R$_{18}$, OR$_{19}$, COR$_{20}$, or a C$_1$–C$_6$alkyl, C$_2$–C$_6$alkenyl, C$_2$–C$_6$alkynyl, C$_3$–C$_7$cycloalkyl, 5- to 7-membered cycloheteroalkyl ring system containing 1 or 2 heteroatoms selected from N, O or S optionally containing one double bond, aryl or 5- to 10-membered heteroaryl ring system containing 1, 2 or 3 heteroatoms selected from N, O or S group each optionally substituted;

R$_{11}$, R$_{12}$, R$_{13}$, R$_{16}$, R$_{19}$ and R$_{20}$ are each independently H or a C$_1$–C$_6$alkyl, C$_2$–C$_6$alkenyl, C$_2$–C$_6$alkynyl, C$_3$–C$_6$cycloalkyl, 5- to 7-membered cycloheteroalkyl ring system containing 1 or 2 heteroatoms selected from N, O or S optionally containing one double bond, aryl or 5- to 10-membered heteroaryl ring system containing 1, 2 or 3 heteroatoms selected from N, O or S group each optionally substituted;

R$_{14}$ and R$_{15}$ are each independently H or an optionally substituted C$_1$–C$_6$alkyl group or R$_{14}$ and R$_{15}$ may be taken together with the atom to which they are attached to form a 5- to 7-membered ring optionally containing another heteroatom selected from O, NR$_{22}$ or S;

R$_{17}$ and R$_{18}$ are each independently H or an optionally substituted C$_1$–C$_4$alkyl group or R$_{17}$ and R$_{18}$ may be taken together with the atom to which they are attached to form a 5- to 7-membered ring optionally containing another heteroatom selected from O, NR$_{21}$ or SO$_x$;

R$_{21}$ and R$_{22}$ are each independently H or a C$_1$–C$_6$alkyl, C$_2$–C$_6$alkenyl, C$_3$–C$_7$cycloalkyl, 5- to 7-membered cycloheteroalkyl ring system containing 1 or 2 heteroatoms selected from N, O or S optionally containing one double bond, aryl or 5- to 10-membered heteroaryl ring system containing 1, 2 or 3 heteroatoms selected from N, O or S group each optionally substituted; and m, p and x are each independently 0 or an integer of 1 or 2; or a pharmaceutically acceptable salt thereof.

11. The composition according to claim 10 having the formula I compound wherein W or Z is N.

12. The composition according to claim 11 having the formula I compound wherein n is 2 and R$_3$ and R$_4$ are H.

13. The composition according to claim 12 having the formula I compound wherein R$_1$ is optionally substituted phenyl, naphthyl or imidazothiazolyl and R$_2$ is H.

14. The composition according to claim 10 having the formula I compound selected from the group consisting of:

2-[3-(phenylsulfonyl)-1H-pyrrolo[2,3-b]pyridin-1-yl]ethylamine;

2-[3-(phenylsulfonyl)-1H-pyrrolo[2,3-c]pyridin-1-yl]ethylamine;

2-[3-(phenylsulfonyl)-1H-pyrrolo[3,2-c]pyridin-1-yl]ethylamine;

2-{3-[(4-fluorophenyl)sulfonyl]-1H-pyrrolo[3,2-b]pyridin-1-yl}ethylamine;

2-{3-[(4-methylphenyl)sulfonyl]-1H-pyrrolo[2,3-b]pyridin-1-yl}ethylamine;

2-[3-(naphth-1-yl)sulfonyl)-1H-pyrrolo[2,3-b]pyridin-1-yl]ethylamine;

2-{3-[(6-chloro-imidazo[2,1-b][1,3]thiazol-5-yl)sulfonyl]-1H-pyrrolo[2,3-b]pyridin-1-yl}ethylamine;

2-{3-[(3-chlorophenyl)sulfonyl]-1H-pyrrolo[2,3-b]pyridin-1-yl}ethylamine;

2-{3-[(2-chlorophenyl)sulfonyl]-1H-pyrrolo[2,3-c]pyridin-1-yl}ethylamine;

2-{3-[(3-methoxyphenyl)sulfonyl]-1H-pyrrolo[3,2-c]pyridin-1-yl}ethylamine;

2-{3-[(4-fluorophenyl)sulfonyl]-1H-pyrrolo[3,2-b]pyridin-1-yl}ethylamine;

N,N-dimethyl-N-(2-{3-[(3-fluorophenyl)sulfonyl]-1H-pyrrolo[2,3-b]pyridin-1-yl}ethyl)amine;

N,N-dimethyl-N-{2-[3-(naphth-1-ylsulfonyl)-1H-pyrrolo[2,3-b]pyridin-1-yl]ethyl}amine;

N,N-dimethyl-N-(2-{3-[(6-chloroimidazo[1,2-b][1,3]thiazol-5-yl)sulfonyl]-1H-pyrrolo[2,3-b]pyridin-1-yl}ethyl)amine;

N,N-dimethyl-N-(2-{3-[(3-chlorophenyl)sulfonyl]-1H-pyrrolo[2,3-b]pyridine-1-yl}ethyl)amine;

3-[3-(phenylsulfonyl)-1H-pyrrolo[2,3-b]pyridin-1-yl]propan-1-amine;

3-[3-(phenylsulfonyl)-1H-pyrrolo[2,3-c]pyridin-1-yl]propan-1-amine;

3-[3-(phenylsulfonyl)-1H-pyrrolo[3,2-c]pyridin-1-yl]propan-1-amine;

3-{3-[(4-fluorophenyl)sulfonyl]-1H-pyrrolo[3,2-b]pyridin-1-yl}propan-1-amine;

2-{6-chloro-3-[(3-chlorophenyl)sulfonyl]-1H-pyrrolo[2,3-b]pyridin-1-yl}ethylamine;

2-{7-chloro-3-[(2-chlorophenyl)sulfonyl]-1H-pyrrolo[2,3-c]pyridin-1-yl}ethylamine;

4-{3-[(3-methoxyphenyl)sulfonyl]-1H-pyrrolo[3,2-c]pyridin-1-yl}butan-1-amine;

4-{3-[(4-fluorophenyl)sulfonyl]-1H-pyrrolo[3,2-b]pyridin-1-yl}butan-1-amine;

N,N-dimethyl-N-{2-[3-(phenylsulfonyl)-1H-pyrrolo[2,3-c]pyridin-1-yl]ethyl}amine;

N,N-dimethyl-N-{2-[3-(phenylsulfonyl)-1H-pyrrolo[3,2-c]pyridin-1-yl]ethyl}amine;

N,N-dimethyl-N-{2-[3-(thien-2-yl)-1H-pyrrolo[2,3-b]pyridin-1-yl]ethyl}amine;

N,N-dimethyl-N-{2-[3-(naphth-1-yl)-1H-pyrrolo[2,3-b]pyridin-1-yl]ethyl}amine;

N,N-dimethyl-N-(2-{3-[(4-fluorophenyl)sulfonyl]-1H-pyrrolo[3,2-b]pyridin-1-yl}ethyl)amine;

N-methyl-N-(2-{3-[(3-chlorophenyl)sulfonyl]-1H-pyrrolo[2,3-b]pyridin-1-yl}ethyl)amine;

N-methyl-N-(2-{3-[(3-fluorophenyl)sulfonyl]-1H-pyrrolo[2,3-b]pyridin-1-yl}ethyl)amine;

N-methyl-N-{2-[3-(naphth-1-ylsulfonyl)-1H-pyrrolo[2,3-b]pyridin-1-yl]ethyl}amine;

N-methyl-N-(2-{3-[(6-chloroimidazo[1,2-b][1,3]thiazol-5-yl)sulfonyl]-1H-pyrrolo[2,3-b]pyridin-1-yl}ethyl)amine;

N-methyl-N-(2-{3-[(2-chlorophenyl)sulfonyl]-1H-pyrrolo[2,3-c]pyridin-1-yl}ethyl)amine;

N-methyl-N-(2-{3-[(3-methoxyphenyl)sulfonyl]-1H-pyrrolo[3,2-c]pyridin-1-yl}ethyl)amine;

N-benzyl-N-(2-{3-[(4-fluorophenyl)sulfonyl]-1H-pyrrolo[3,2-b]pyridin-1-yl}ethyl)amine;

N,N-dibenzyl-3-[3-(phenylsulfonyl)-1H-pyrrolo[2,3-b]pyridin-1-yl]propan-1-amine;

3-[3-(phenylsulfonyl)-1H-pyrrolo[2,3-c]pyridin-1-yl]propan-1-amine;

3-[3-(phenylsulfonyl)-1H-pyrrolo[3,2-c]pyridin-1-yl]propan-1-amine; and the pharmaceutically acceptable salts thereof.

15. A process for the preparation of a compound of formula I

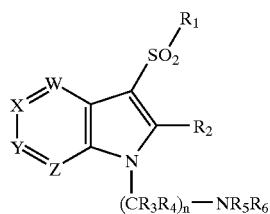
(I)

wherein
W is N or $CR_7$;
X is N or $CR_8$;
Y is N or $CR_9$;
Z is N or $CR_{10}$ with the proviso that only one of W, X, Y and Z must be N;
n is an integer of 2, 3, 4 or 5;
$R_1$ is an optionally substituted $C_1$–$C_6$alkyl, $C_3$–$C_7$cycloalkyl, aryl, or 5- to 10-membered heteroaryl ring system containing 1, 2 or 3 heteroatoms selected from N, O or S group or an optionally substituted 8- to 13-membered bicyclic or tricyclic ring system having a N atom at the bridgehead and optionally containing 1, 2 or 3 additional heteroatoms selected from N, O or S;
$R_2$ is H, halogen, or a $C_1$–$C_6$alkyl, $C_1$–$C_6$alkoxy, $C_3$–$C_7$cycloalkyl, aryl or 5- to 10-membered heteroaryl ring system containing 1, 2 or 3 heteroatoms selected from N, O or S group each optionally substituted;
$R_3$ and $R_4$ are each independently H or an optionally substituted $C_1$–$C_6$alkyl group;
$R_5$ and $R_6$ are each independently H or a $C_1$–$C_6$alkyl, $C_2$–$C_6$alkenyl, $C_2$–$C_6$alkynyl, $C_3$–$C_7$cycloalkyl, 5- to 7-membered cycloheteroalkyl ring system containing 1 or 2 heteroatoms selected from N, O or S optionally containing one double bond, aryl or 5- to 10-membered heteroaryl ring system containing 1, 2 or 3 heteroatoms selected from N, O or S group each optionally substituted or $R_5$ and $R_6$ may be taken together with the atom to which they are attached to form an optionally substituted 5- to 8-membered ring optionally containing an additional heteroatom selected from O, $NR_{11}$ or $SO_m$;
$R_7$, $R_8$, $R_9$ and $R_{10}$ are independently H, halogen, CN, $OCO_2R_{12}$, $CO_2R_{13}$, $CONR_{15}$, $SO_pR_{16}$, $NR_{17}R_{18}$, $OR_{19}$, $COR_{20}$, or a $C_1$–$C_6$alkyl, $C_2$–$C_6$alkenyl, $C_2$–$C_6$alkynyl, $C_3$–$C_7$cycloalkyl, 5- to 7-membered cycloheteroalkyl ring system containing 1 or 2 heteroatoms selected from N, O or S optionally containing one double bond, aryl or 5- to 10-membered heteroaryl ring system containing 1, 2 or 3 heteroatoms selected from N, O or S group each optionally substituted;
$R_{11}$, $R_{12}$, $R_{13}$, $R_{16}$, $R_{19}$ and $R_{20}$ are each independently H or a $C_1$–$C_6$alkyl, $C_2$–$C_6$alkenyl, $C_2$–$C_6$alkynyl, $C_3$–$C_6$cycloalkyl, 5- to 7-membered cycloheteroalkyl ring system containing 1 or 2 heteroatoms selected from N, O or S optionally containing one double bond, aryl or 5- to 10-membered heteroaryl ring system containing 1, 2 or 3 heteroatoms selected from N, O or S group each optionally substituted;
$R_{14}$ and $R_{15}$ are each independently H or an optionally substituted $C_1$–$C_6$alkyl group or $R_{14}$ and $R_{15}$ may be taken together with the atom to which they are attached to form a 5- to 7-membered ring optionally containing another heteroatom selected from O, $NR_{22}$ or S;
$R_{17}$ and $R_{18}$ are each independently H or an optionally substituted $C_1$–$C_4$alkyl group or $R_{17}$ and $R_{18}$ may be taken together with the atom to which they are attached to form a 5- to 7-membered ring optionally containing another heteroatom selected from O, $NR_{21}$ or $SO_x$;
$R_{21}$ and $R_{22}$ are each independently H or a $C_1$–$C_6$alkyl, $C_2$–$C_6$alkenyl, $C_3$–$C_7$cycloalkyl 5- to 7-membered cycloheteroalkyl ring system containing 1 or 2 heteroatoms selected from N, O or S optionally containing one double bond, aryl or 5- to 10-membered heteroaryl ring system containing 1, 2 or 3 heteroatoms selected from N, O or S group each optionally substituted; and
m, p and x are each independently 0 or an integer of 1 or 2 which process comprises reacting a compound of formula II

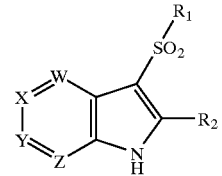
(II)

wherein W, X, Y, Z, $R_1$ and $R_2$ are as described hereinabove with a haloalkylamine of formula III Hal—$(CR_3R_4)_n$—$NR_5R_6$ (III)

wherein Hal represents Cl, Br or I and $R_3$, $R_4$, $R_5$, $R_6$ and n are as described hereinabove in the presence of a base optionally in the presence of a solvent.

* * * * *